(12) United States Patent
Madrid et al.

(10) Patent No.: US 9,663,478 B2
(45) Date of Patent: May 30, 2017

(54) **BENZOTRIAZINE OXIDES AS DRUGS TARGETING *MYCOBACTERIUM TUBERCULOSIS***

(71) Applicants: Peter Madrid, Saratoga, CA (US); Sidharth Chopra, Mountain View, CA (US); Kenneth Ryan, Sunnyvale, CA (US); Gary Koolpe, Tracy, CA (US)

(72) Inventors: Peter Madrid, Saratoga, CA (US); Sidharth Chopra, Mountain View, CA (US); Kenneth Ryan, Sunnyvale, CA (US); Gary Koolpe, Tracy, CA (US)

(73) Assignee: SRI INTERNATIONAL, Menlo Park, CA (US)

( * ) Notice: Subject to any disclaimer, the term of this patent is extended or adjusted under 35 U.S.C. 154(b) by 527 days.

(21) Appl. No.: 13/726,135

(22) Filed: Dec. 23, 2012

(65) Prior Publication Data
US 2013/0150369 A1     Jun. 13, 2013

Related U.S. Application Data

(63) Continuation of application No. PCT/US2012/068636, filed on Dec. 7, 2012.

(60) Provisional application No. 61/567,829, filed on Dec. 7, 2011.

(51) Int. Cl.

| | | |
|---|---|---|
| *C07D 253/10* | (2006.01) | |
| *A61K 31/53* | (2006.01) | |
| *A61P 31/06* | (2006.01) | |
| *C07D 403/12* | (2006.01) | |
| *C07D 401/04* | (2006.01) | |
| *C07D 401/12* | (2006.01) | |
| *C07D 403/04* | (2006.01) | |
| *A61K 31/5377* | (2006.01) | |
| *A61K 31/541* | (2006.01) | |
| *A61K 45/06* | (2006.01) | |
| *C07D 413/04* | (2006.01) | |
| *C07D 417/04* | (2006.01) | |

(52) U.S. Cl.
CPC ........... *C07D 253/10* (2013.01); *A61K 31/53* (2013.01); *A61K 31/5377* (2013.01); *A61K 31/541* (2013.01); *A61K 45/06* (2013.01); *C07D 401/04* (2013.01); *C07D 401/12* (2013.01); *C07D 403/04* (2013.01); *C07D 403/12* (2013.01); *C07D 413/04* (2013.01); *C07D 417/04* (2013.01)

(58) Field of Classification Search
CPC .............................. C07D 253/10; A61K 31/53
USPC ........................................... 544/183; 514/243
See application file for complete search history.

(56) References Cited

U.S. PATENT DOCUMENTS

| | | | |
|---|---|---|---|
| 3,868,371 A | | 2/1975 | Ley |
| 3,980,779 A | * | 9/1976 | Ley et al. ..................... 514/243 |
| 3,991,189 A | * | 11/1976 | Seng et al. .................... 514/243 |
| 4,001,410 A | * | 1/1977 | Ley et al. ..................... 514/243 |
| 6,277,835 B1 | | 8/2001 | Brown |
| 7,989,451 B2 | * | 8/2011 | Hay et al. ..................... 514/243 |
| 2009/0186886 A1 | * | 7/2009 | Hay et al. .................. 514/232.8 |

OTHER PUBLICATIONS

Hay et al. J. Med. Chem. 2003, 46, 169-182.*
International Search Report & Written Opinion in PCT/US12/68636.

* cited by examiner

*Primary Examiner* — Venkataraman Balasubramanian
(74) *Attorney, Agent, or Firm* — Richard Aron Osman

(57) ABSTRACT

Benzotriazine doxides are disclosed as drugs targeting *mycobacterium tuberculosis*, including novel compounds of formula I:

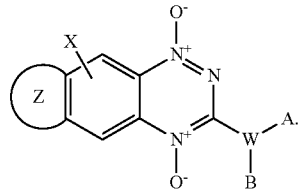

19 Claims, 1 Drawing Sheet

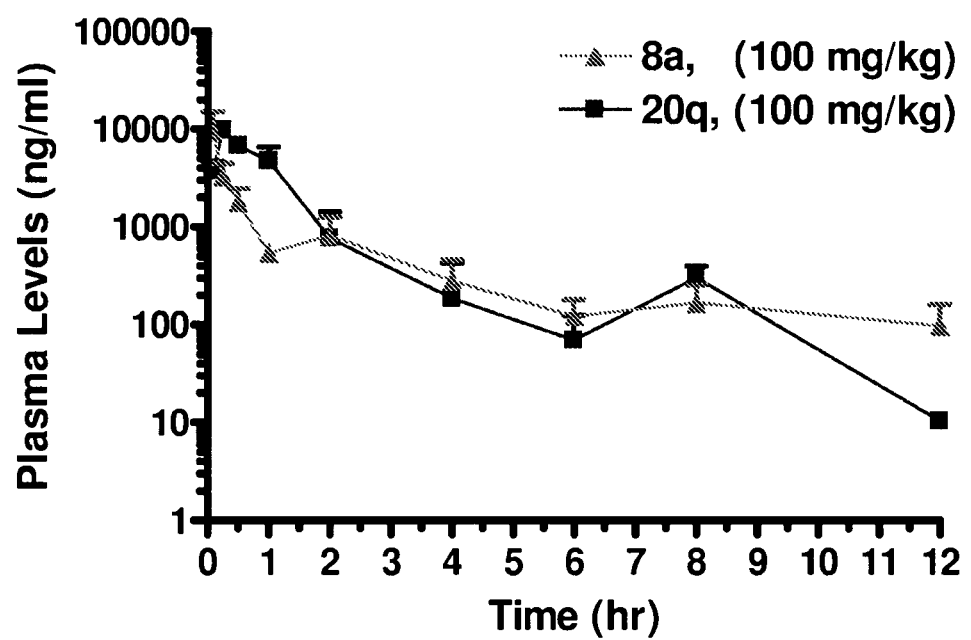

BENZOTRIAZINE OXIDES AS DRUGS TARGETING *MYCOBACTERIUM TUBERCULOSIS*

This application claims priority to PCT/US12/68636, filed: Dec. 7, 2012, which claims priority to U.S. 61/567,829 filed Dec. 7, 2011.

This invention was made with government support under NIH Contract No. HHSN266200600011C and NIH Grant No. 1R56A109081-017 awarded by National Institutes of Health (NIH); the government has certain rights in the invention.

INTRODUCTION

The current R&D pipeline for new tuberculosis (TB) drugs is inadequate to address emerging drug-resistant strains. Accordingly, filling the early drug development pipeline with novel therapies likely to slow additional drug resistance is urgent. Combination chemotherapy has been a standard of care for TB since the 1950s, when it was shown that combining drugs slowed the development of drug resistance, particularly for bactericidal compounds.1 The next major breakthrough in TB treatment was the inclusion of rifampin and pyrazinamide in the multidrug cocktail because those drugs significantly accelerated the clearance of the infection, presumably through their bactericidal activity against the populations of bacterial persisters. The currently recommended Direct Observed Therapy Short-course (DOTS) regimen, has been shown to be highly effective in treating drug-sensitive TB, but requires at least 6 months of treatment. The next major breakthrough in the treatment of TB is likely to be the development of an improved regimen that requires less treatment time, thus decreasing cost, increasing patient compliance, and slowing the emergence of multidrug-resistant TB (MDR-TB) strains.

*Mycobacterium tuberculosis* (Mtb) survival in stages of nonreplicating persistence (NRP) that are tolerant to many drugs provides a possible explanation for the long treatment regimens required to eliminate an infection.2 The development of new combination therapy regimens, including drugs that are bactericidal against these NRP stages of Mtb, has the potential for shortening the length of treatment regimens. Metronidazole, a 5-nitroimidazole antibiotic primarily used for the treatment of anaerobic bacterial infections, was one of the first compounds shown to be bactericidal against NRP Mtb.2 Two newer 5-nitroimidazoles, PA-8243 and OPC-676834, have greater potencies against Mtb and are being evaluated clinically in combinations with standard TB drugs. So far, both of these 5-nitroimidazoles have been shown to have early bactericidal activity in patients.5,6 Preclinical studies in murine models of TB indicate that including bactericidal drugs with activity against NRP Mtb in a combination regimen shortens the time required to cure mice of the infection,7 but it remains to be determined whether these findings will translate to the ability to shorten the length of clinical treatment regimens.

To develop new drugs that shorten TB treatment, we evaluated additional classes of bioreductively-activated compounds with previously reported antimicrobial activities for their activities against Mtb H37Rv. We disclose BTOs as a new class of antitubercular compounds with many unique properties that make them well-suited as anti-TB drugs, particularly with the potential to shorten the length of treatment.

Relevant literature includes: Chopra et al, J Med. Chem. 2012 Jul. 12; 55(13):6047-60; Hay, et al., J. Med. Chem., 2008, 51 (21), pp 6853-6865; Zeman, et al., Int. J. Radiat. Oncol., Biol., Phys. 1989, 16, 977-981; Minchinton, et al, Int. J. Radiat. Oncol., Biol., Phys 1992, 22, 701-705; Kelson, et al., Anti-Cancer Drug Des. 1998, 13, 575-592; Jiang, et al., Bioorg. Med. Chem. Lett. 2006, 16, 4209-4213; and Jiang, et al, Arch. Pharm. (Weinheim, Ger.) 2007, 340, 258-263.

SUMMARY OF THE INVENTION

In one embodiment the invention provides compounds having the structure of formula I:

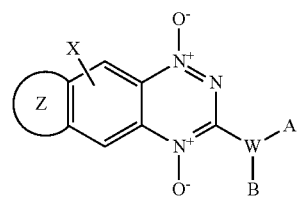

wherein: each X is independently H, halogen, alkyl, OR, SR, NR'R, BR'R, heterocycles, or another functional group, wherein each R is independently H, halogen, alkyl, or another functional group; W is N, C, O, S, H or B or another linking atom; each A and B is H or optionally substituted alkyl, which may be joined in an optionally hetero-, cycloalkyl; and Z is an optionally present, optionally substituted 4-8 membered ring, saturated or unsaturated, fused to the bezotriazine ring at either the 6,7-, 5,6- or 7,8-position, or a pharmaceutically acceptable salt or stereoisomer thereof.

In particular embodiments each X is independently H, halogen, alkyl, OR, SR, NR'R, BR'R, wherein each R is independently H, halogen or alkyl, more particularly H; W is N, C, O, S, or B, more particularly N; each A and B is H or optionally substituted alkyl, which may be joined in an optionally hetero-, cycloalkyl, more particularly an optionally substituted piperidinyl or pyrrolidinyl; and Z is an optionally present, optionally substituted 4-8 membered ring, saturated or unsaturated, fused to the bezotriazine ring at either the 6,7-, 5,6- or 7,8-position, particularly an optionally present, optionally substituted 5 or 6-membered ring, saturated or unsaturated, fused to the bezotriazine ring at the 7,8-position, more particularly a present, 5-membered ring, unsaturated, fused to the bezotriazine ring at the 7,8-position.

In particular embodiments:
each X is independently H, halogen, alkyl, OR, SR, NR'R, or BR'R, wherein each R is independently H, halogen, or alkyl; W is N, C, O, S or B; each A and B is H or optionally substituted alkyl, which may be joined in an optionally hetero-, cycloalkyl; and Z is an optionally present, optionally substituted 4-8 membered ring, saturated or unsaturated, fused to the bezotriazine ring at either the 6,7-, 5,6- or 7,8-position.

each X is independently H, halogen, alkyl, OR, SR, NR'R, or BR'R, wherein each R is independently H, halogen, or alkyl; W is N, C, O, S or B; each A and B is optionally substituted alkyl, which may be joined in an optionally hetero-, cycloalkyl; and Z is an optionally present, optionally substituted 4-8 membered ring, saturated or unsaturated, fused to the bezotriazine ring at either the 6,7-, 5,6- or 7,8-position.

each X is independently H, halogen, alkyl, OR, SR, NR'R, or BR'R, wherein each R is independently H, halogen, or alkyl; W is N; each A and B is optionally substituted alkyl, which may be joined in a heterocycloalkyl; and Z is an optionally present, optionally substituted 5 or 6-membered ring, saturated or unsaturated, fused to the bezotriazine ring at the 7,8-position;

each X is H; W is N; A and B are joined in an optionally substituted piperidinyl or pyrrolidinyl; and Z is a 5-membered ring, unsaturated, fused to the bezotriazine ring at the 7,8-position.

In particular embodiments the compound is a BTO of a particularly recited structure disclosed herein, such as in the tables below.

In other embodiments the invention provides pharmaceutical compositions and kits comprising a subject BTO compound and a second, different anti-*mycobacterium tuberculosis* (Mtb) drug.

The invention also provides methods of making subject BTO compounds comprising an oxidation reaction using HOF:ACN.

The invention also provides methods of treating a *mycobacterium tuberculosis* (Mtb) infection, comprising: contacting a person in need thereof with an effective amount of a subject compound or composition.

In another aspect the invention provides methods method of treating a *mycobacterium tuberculosis* (Mtb) infection, comprising: contacting a person in need thereof with an effective amount of a 1,2,4-benzotriazine di-N-oxide (BTO).

The subject methods of use or treatment may further comprise a subsequent step of detecting a resultant diminution in the infection and/or a prior step of detecting the infection.

In particular embodiments, the infection comprises non-replicating persistence (NRP) Mtb cells.

The invention encompasses all combinations of particular and preferred embodiments as though each had been laboriously, separately recited.

BRIEF DESCRIPTION OF THE DRAWING

FIGURE. Plasma drug concentrations of 8a and 20q in female Balb/c mice (n=3 mice per time point) after po administration of 100 mg/kg of each compound. Blood was collected at time points through 24 hr post-dose, processed to plasma and analyzed for each of the test compounds. The concentrations at the 24 hr time point for both compounds was lower than the limit of quantitation.

DESCRIPTION OF PARTICULAR EMBODIMENTS OF THE INVENTION

The following descriptions of particular embodiments and examples are provided by way of illustration and not by way of limitation. Those skilled in the art will readily recognize a variety of noncritical parameters that could be changed or modified to yield essentially similar results. Unless contraindicated or noted otherwise, in these descriptions and throughout this specification, the terms "a" and "an" mean one or more, the term "or" means and/or and polynucleotide sequences are understood to encompass opposite strands as well as alternative backbones described herein. Furthermore, genuses are recited as shorthand for a recitation of all members of the genus; for example, the recitation of (C1-C3) alkyl is shorthand for a recitation of all C1-C3 alkyls: methyl, ethyl and propyl, including isomers thereof.

The invention provides compounds of formula I, and subgenera and species thereof, compositions, including formulations and kits, containing such compounds, and methods of making and using the disclosed compounds and compositions.

The invention also provides novel methods for preparing these compounds by the oxidation of the compounds using HOF ACN:

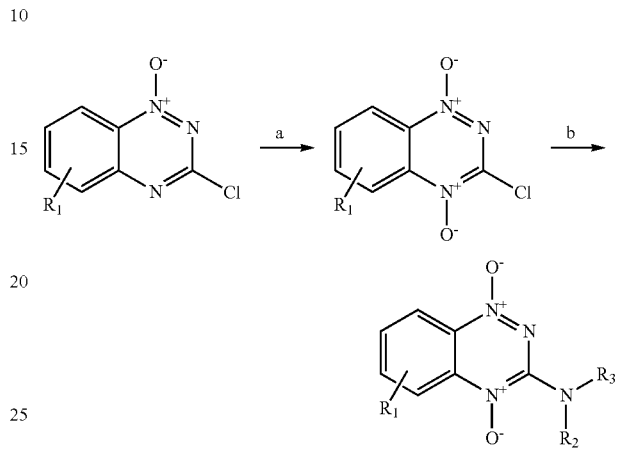

Reagents and Conditions: a) HOF•ACN, DCM, -15° C., 30 min. b) HNR$_2$R$_3$, Et$_3$N, DCM.

The activity of these compounds against *M. tuberculosis* has been determined using a minimum inhibitory concentration (MIC) measurement. The toxicity and selectivity of the compounds have been quantified by a 50% cytotoxicity concentration (CC$_{50}$) using a Vero cell viability assay with the Promega Cell Titer Glo reagent. The activity against non-replicating *M. tuberculosis* has been measured using the published Low-Oxygen Recovery Assay (LORA). The Selectivity Index (SI) of each compound was measured as the ratio of the CC$_{50}$/TB-MIC values.

TABLE P1

Anti-TB activity of side chain substituted Benzotriazine Oxides.

| Compound | TB MIC -SRI | VERO Tox (CC$_{50}$) | TB MIC - UIC | LORA MIC | SI |
|---|---|---|---|---|---|
| SRI-003356 | 1.25 | | | | |
| SRI-012255 | 2.5 | 20.7 | 1.82 | 1.76 | 8.3 |
| SRI-012256 | 2.5 | 7.9 | 1.64 | 0.5 | 3.2 |
| SRI-012257 | 0.625 | 2.3 | 0.22 | <0.125 | 3.7 |
| SRI-012258 | 5.0 | 26.3 | 1.95 | 0.99 | 5.3 |
| SRI-012259 | 1.25 | 4.1 | 0.52 | 0.38 | 3.3 |
| SRI-012260 | 1.25 | 8.9 | 0.94 | 0.84 | 7.1 |
| SRI-012261 | 1.25 | 8.9 | 0.92 | 0.36 | 7.1 |
| SRI-012262 | 2.5 | 21.6 | 2.0 | 1.28 | 8.6 |
| SRI-012263 | 2.5 | 11.7 | 1.98 | 0.83 | 4.7 |
| SRI-012264 | 0.625 | 3.4 | 0.6 | 0.42 | 5.5 |
| SRI-012265 | 2.5 | 10.4 | 3.58 | 0.68 | 4.2 |
| SRI-012266 | 2.5 | 8.9 | 3.77 | 0.75 | 3.6 |
| SRI-012267 | 5.0 | 21.0 | 1.93 | 0.98 | 4.2 |
| SRI-012268 | 5.0 | 20.2 | 2.43 | 1.0 | 4.0 |
| SRI-012269 | 2.5 | 7.3 | 1.91 | 2.33 | 2.9 |
| SRI-012270 | 1.25 | 5.2 | 0.57 | 0.39 | 4.2 |
| SRI-012271 | 5.0 | 36.5 | 3.63 | 1.94 | 7.3 |
| SRI-012272 | 10.0 | 50.0 | 6.57 | 4.87 | 5.0 |
| SRI-012273 | 1.25 | 4.6 | 0.48 | 0.48 | 3.7 |

TABLE P2

Anti-TB activity of ring substituted Benzotriazine Oxides.

| Compound | TB MIC - SRI | VERO Tox-SRI | TB MIC - UIC | LORA MIC | SI |
|---|---|---|---|---|---|
| SRI-012274 | 0.312 | 3.5 | 0.93 | 2.80 | 11.4 |
| SRI-012275 | 0.625 | <2.5 | 0.68 | 0.47 | <4 |
| SRI-012276 | 0.312 | 2.5 | 0.40 | 0.88 | 8.0 |
| SRI-012277 | 0.312 | 2.3 | 0.33 | 0.34 | 7.3 |
| SRI-012278 | 5 | 6.3 | 2.00 | 1.87 | 1.3 |
| SRI-012279 | 1.25 | 4.4 | 0.49 | 0.71 | 3.5 |
| SRI-012280 | 0.312 | <2.5 | <0.125 | 0.21 | <4 |
| SRI-012281 | 1.25 | <2.5 | 0.55 | 0.40 | <4 |
| SRI-012282 | 0.625 | <2.5 | 0.39 | 0.21 | <4 |
| SRI-012283 | 1.25 | <2.5 | 0.50 | 0.42 | <4 |
| SRI-012284 | 0.625 | 4.6 | 0.35 | 0.75 | 7.3 |
| SRI-012285 | 2.5 | 15.8 | 15.14 | 16.16 | 6.3 |
| SRI-012286 | 1.25 | 36.0 | 0.95 | 0.83 | 28.8 |
| SRI-012301 | 0.625 | 1.36 | 0.21 | 0.22 | 2.2 |
| SRI-012302 | 0.156 | 1.6 | <0.125 | <0.125 | 10.3 |
| SRI-012303 | 0.625 | 2.62 | 0.94 | 0.63 | 4.2 |
| SRI-012304 | 1.25 | 2.6 | 1.46 | 0.78 | 2.1 |
| SRI-012305 | 0.156 | | <0.125 | 0.20 | |
| SRI-012306 | 1.25 | 2.65 | <0.125 | 0.41 | 2.1 |
| SRI-012396 | 1.25 | | | | |
| SRI-012397 | 0.625 | | | | |
| SRI-012398 | 2.5 | | | | |
| SRI-012399 | 2.5 | | | | |
| SRI-012401 | 0.312 | | | | |
| SRI-012402 | 0.312 | | | | |
| SRI-012403 | 0.625 | 33.6 | | 53.8 | |
| SRI-012404 | 1.25 | 50 | | 40 | |
| SRI-012405 | 0.312 | 21.57 | | 69.1 | |
| SRI-012405 | 0.625 | 22.5 | | 36.0 | |
| SRI-012459 | 0.625 | 21.8 | | 34.9 | |
| SRI-012460 | 0.312 | 21.8 | | 69.9 | |
| SRI-012461 | 0.156 | 2.3 | | 14.7 | |
| SRI-012462 | 0.625 | | | | |
| SRI-012463 | 0.625 | 9.85 | | 15.8 | |
| SRI-012464 | 0.625 | | | | |
| SRI-012465 | 0.156 | | | | |
| SRI-012466 | 0.156 | | | | |
| SRI-012467 | 0.312 | 0.81 | | | 2.6 |
| SRI-012468 | 2.5 | 100 | | | 40 |
| SRI-012469 | 2.5 | 50 | | | 20.0 |
| SRI-012470 | 5 | 50 | | | 10.0 |
| SRI-012473 | 0.312 | 3.7 | | | 11.9 |
| SRI-012496 | 1.25 | 21.78 | | | 17.4 |
| SRI-012497 | 1.25 | 50 | | | 40.0 |
| SRI-012498 | 1.25 | 50 | | | 40.0 |

TABLE P3

Anti-TB activity of di-N-alkyl Benzotriazine Oxides.

| Compound | TB MIC - SRI | TB MIC - UIC | LORA MIC | VERO Tox | SI |
|---|---|---|---|---|---|
| SRI-003270 | 2.5 | 5.4 | | | 2.2 |
| SRI-009728 | 0.312 | 12.4 | | | 39.6 |
| SRI-012495 | 0.312 | 17.42 | | | 55.8 |
| SRI-012530 | 0.625 | | | | |
| SRI-012562 | 0.625 | | | | |
| SRI-012563 | 0.625 | | | | |
| SRI-012564 | 0.312 | | | | |
| SRI-012565 | 0.312 | | | | |
| SRI-012566 | 5 | | | | |
| SRI-012567 | 1.25 | | | | |
| SRI-012568 | 5 | | | | |

TABLE P4

Activity of Compounds Against Drug-Resistant *M. tuberculosis* strains.

| | | Mtb Strains Resistant to | | | | | |
|---|---|---|---|---|---|---|---|
| Compounds | H37Rv | Streptomycin ATCC 35820 | P-aminosalicyclic acid ATCC 35821 | Isoniazid ATCC 35822 | Kanamycin ATCC 35827 | Ethionamide ATCC 35830 | Ethambutol ATCC 35837 |
| SRI-003270 | 1.25 | 0.31 | 1.25 | 1.25 | 1.25 | 0.31 | 0.63 |
| SRI-003274 | 1.25 | 1.25 | 1.25 | 1.25 | 1.25 | 1.25 | 1.25 |
| SRI-012495 | 0.31 | 0.02 | 0.62 | 0.31 | 0.31 | 0.31 | 0.31 |
| SRI-012496 | 1.25 | 1.25 | 1.25 | 1.25 | 1.25 | 1.25 | 1.25 |
| SRI-012497 | 1.25 | 1.25 | 1.25 | 2.5 | 2.5 | 1.25 | 2.5 |
| SRI-012498 | 1.25 | 1.25 | 1.25 | 2.5 | 1.25 | 1.25 | 1.25 |
| SRI-009728 | 0.31 | 0.31 | 0.31 | 0.31 | 0.31 | 0.16 | 0.31 |
| SRI-012530 | 0.62 | 0.16 | 0.31 | 0.31 | 0.63 | 0.62 | 0.62 |
| SRI-012403 | 0.62 | 0.31 | 0.62 | 1.25 | 1.25 | 0.62 | 0.62 |
| SRI-012405 | 0.62 | 0.16 | 0.31 | 0.62 | 0.62 | 0.31 | 0.62 |
| SRI-012286 | 1.25 | 0.63 | 1.25 | 2.5 | 1.25 | 1.25 | 1.25 |
| SRI-003356 | 2.5 | 1.25 | 1.25 | 2.5 | 2.5 | 1.25 | 2.5 |
| SRI-012562 | 0.62 | 0.15 | 0.31 | 0.15 | 0.31 | 0.31 | 0.31 |
| SRI-012563 | 0.62 | <0.07 | 0.15 | <0.07 | 0.31 | 0.15 | 0.31 |
| SRI-012564 | 0.31 | <0.07 | 0.07 | <0.07 | 0.15 | 0.07 | 0.15 |
| SRI-012565 | 0.31 | <0.07 | 0.15 | 0.07 | 0.15 | 0.15 | 0.31 |
| SRI-012566 | 5 | 2.5 | 2.5 | 2.5 | 2.5 | 0.62 | 2.5 |
| SRI-012567 | 1.25 | 0.31 | 0.62 | 0.31 | 0.62 | 0.31 | 0.62 |
| SRI-012568 | 5 | 2.5 | 2.5 | 2.5 | 2.5 | 0.62 | 2.5 |

TABLE P5

Representative Structures of Compounds.

| Compound | Structure |
|---|---|
| SRI-003356 | benzo[1,2,4]triazine 1,4-dioxide with 3-NH-C(CH₃)₃ (tert-butylamino) |
| SRI-012255 | benzo[1,2,4]triazine 1,4-dioxide with 3-NH-cyclopropyl |
| SRI-012256 | benzo[1,2,4]triazine 1,4-dioxide with 3-NH-cycloheptyl |
| SRI-012257 | benzo[1,2,4]triazine 1,4-dioxide with 3-NH-(4-tert-butylcyclohexyl) |
| SRI-012258 | benzo[1,2,4]triazine 1,4-dioxide with 3-NH-CH(CH₃)CH₂CH₂CH₃ (pentan-2-yl amino) |
| SRI-012259 | benzo[1,2,4]triazine 1,4-dioxide with 3-NH-CH(CH₃)CH₂CH(CH₃)₂ (4-methylpentan-2-yl amino) |
| SRI-012260 | benzo[1,2,4]triazine 1,4-dioxide with 3-NH-cyclobutyl |
| SRI-012261 | benzo[1,2,4]triazine 1,4-dioxide with 3-NH-CH(CH₃)-cyclohexyl, AND Enantiomer |
| SRI-012262 | benzo[1,2,4]triazine 1,4-dioxide with 3-NH-CH(CH₃)CH₂CH₃ (sec-butylamino) |
| SRI-012263 | benzo[1,2,4]triazine 1,4-dioxide with 3-NH-CH(CH₃)CH₂CH(CH₃)₂ |
| SRI-012264 | benzo[1,2,4]triazine 1,4-dioxide with 3-NH-norbornyl, AND Enantiomer |
| SRI-012265 | benzo[1,2,4]triazine 1,4-dioxide with 3-NH-cyclopentyl |
| SRI-012266 | benzo[1,2,4]triazine 1,4-dioxide with 3-NH-cyclohexyl |
| SRI-012267 | benzo[1,2,4]triazine 1,4-dioxide with 3-NH-CH(CH₃)CH(CH₃)₂ (3-methylbutan-2-yl amino) |

TABLE P5-continued

Representative Structures of Compounds.

| Compound | |
|---|---|
| SRI-012268 | (structure) |
| SRI-012269 | AND Enantiomer (structure) |
| SRI-012270 | (structure) |
| SRI-012271 | (structure) |
| SRI-012272 | (structure) |
| SRI-012273 | AND Enantiomer (structure) |
| SRI-012274 | (structure) |
| SRI-012275 | (structure) |
| SRI-012276 | (structure) |
| SRI-012277 | (structure) |
| SRI-012278 | (structure) |
| SRI-012279 | (structure) |
| SRI-012280 | AND Enantiomer (structure) |
| SRI-012281 | (structure) |

TABLE P5-continued
Representative Structures of Compounds.
| Compound | |
|---|---|
| SRI-012282 | 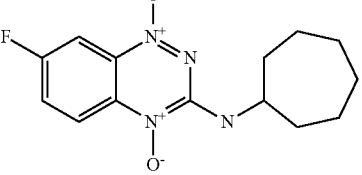 |
| SRI-012283 | 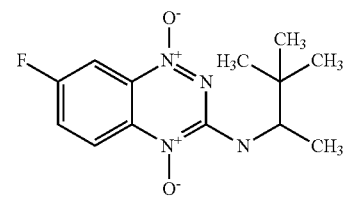 [SMILES: CC(Nc1n[n+]([O-])c2cc(F)ccc2[n+]1[O-])C(C)(C)C] |
| SRI-012284 | 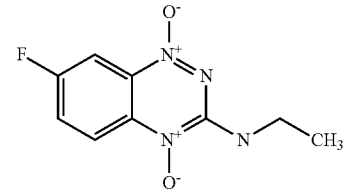 [SMILES: CCNc1n[n+]([O-])c2cc(F)ccc2[n+]1[O-]] |
| SRI-012285 | 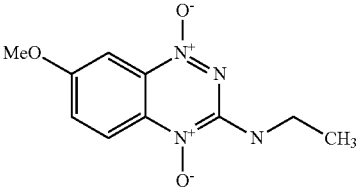 [SMILES: CCNc1n[n+]([O-])c2cc(OC)ccc2[n+]1[O-]] |
| SRI-012286 | 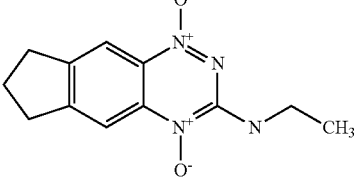 |
| SRI-012301 | 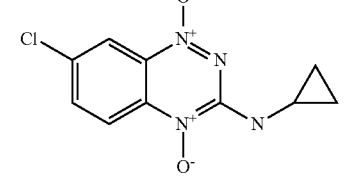 |
| SRI-012302 | 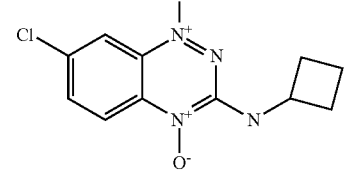 |
| SRI-012303 | 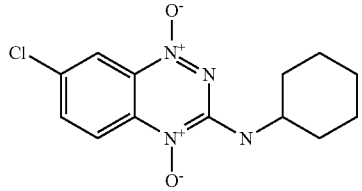 [SMILES: [O-][n+]1nc(NC2CCCCC2)[n+]([O-])c2ccc(Cl)cc21] |
| SRI-012304 | 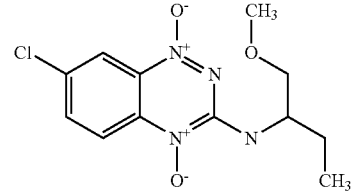 [SMILES: CCC(COC)Nc1n[n+]([O-])c2cc(Cl)ccc2[n+]1[O-]] |
| SRI-012305 | AND Enantiomer 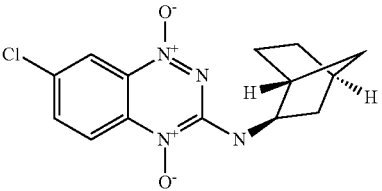 |
| SRI-012306 | 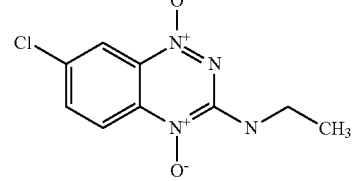 |
| SRI-012396 | 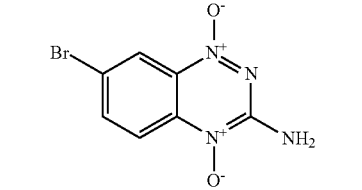 [SMILES: Nc1n[n+]([O-])c2cc(Br)ccc2[n+]1[O-]] |
| SRI-012397 | 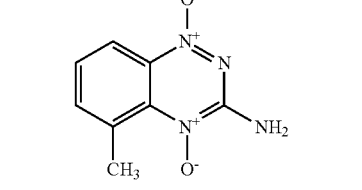 |
| SRI-012398 | 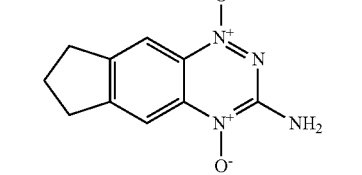 |

TABLE P5-continued

Representative Structures of Compounds.

| Compound | |
|---|---|
| SRI-012399 | (structure) |
| SRI-012401 | (structure) |
| SRI-012402 | AND Enantiomer (structure) |
| SRI-012403 | (structure) |
| SRI-012404 | AND Enantiomer (structure) |
| SRI-012405 | (structure) |
| SRI-012405 | (structure) |
| SRI-012459 | (structure) |
| SRI-012460 | (structure) |
| SRI-012461 | AND Enantiomer (structure) |
| SRI-012462 | (structure) |
| SRI-012463 | (structure) |
| SRI-012464 | (structure) |
| SRI-012465 | (structure) |

TABLE P5-continued

Representative Structures of Compounds.

| Compound | |
|---|---|
| SRI-012466 | |
| SRI-012467 | |
| SRI-012468 | |
| SRI-012469 | |
| SRI-012470 | |
| SRI-012473 | |
| SRI-012496 | |
| SRI-012497 | |
| SRI-012498 | |
| SRI-003270 | |
| SRI-009728 | |
| SRI-012495 | |
| SRI-012530 | |
| SRI-012562 | |

TABLE P5-continued

Representative Structures of Compounds.

| Compound |  |
|---|---|
| SRI-012563 | (structure) |
| SRI-012564 | (structure) |
| SRI-012565 | (structure) |
| SRI-012566 | (structure) |
| SRI-012567 | (structure) |
| SRI-012568 | (structure) |

TABLE E1

Additional BTO Activity Data

| Cmpd # | Reference | Compound Weight | Structure |
|---|---|---|---|
| 1 | SRI-013330 | 368.4386 | (structure) |
| 2 | SRI-013329 | 323.3543 | (structure) |

TABLE E1-continued

Additional BTO Activity Data

| Cmpd # | Reference | Compound Weight | Structure |
|--------|-----------|-----------------|-----------|
| 3 | SRI-013328 | 284.3174 | 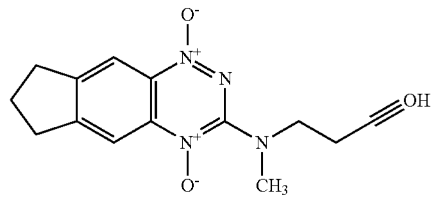 |
| 4 | SRI-013327 | 366.3941 | 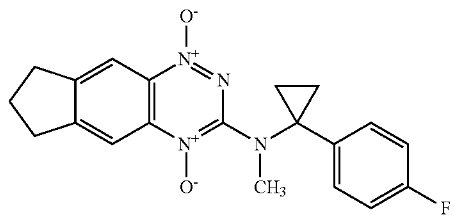 [SMILES: CN(c1n[n+]([O-])c2cc3c(cc2[n+]1[O-])CCC3)C1(c2ccc(F)cc2)CC1] |
| 5 | SRI-013326 | 354.3831 | 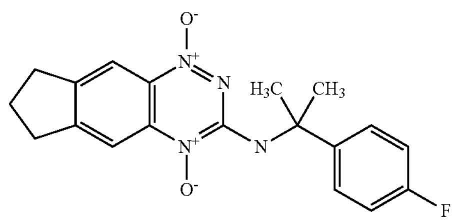 [SMILES: CC(C)(Nc1n[n+]([O-])c2cc3c(cc2[n+]1[O-])CCC3)c1ccc(F)cc1] |
| 6 | SRI-013310 | 270.6749 | 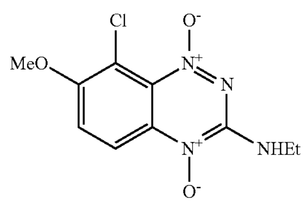 |
| 7 | SRI-013277 | 351.3792 | 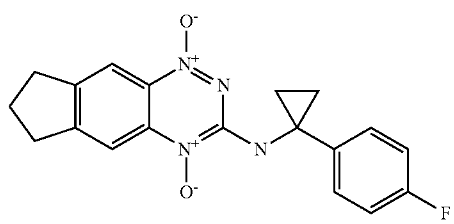 [SMILES: [O-][n+]1nc(NC2(c3ccc(F)cc3)CC2)[n+]([O-])c2cc3c(cc21)CCC3] |
| 8 | SRI-013253 | 436.5092 | 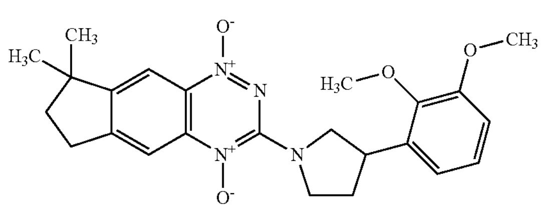 |
| 9 | SRI-013243 | 300.36 | 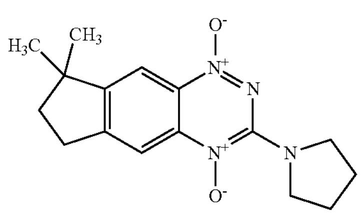 [SMILES: CC1(C)CCc2cc3c(cc21)[n+]([O-])nc(N1CCCC1)[n+]3[O-]] |

TABLE E1-continued

Additional BTO Activity Data

| Cmpd # | Reference | Compound Weight | Structure |
|--------|-----------|-----------------|-----------|
| 10 | SRI-013158 | 312.371 | 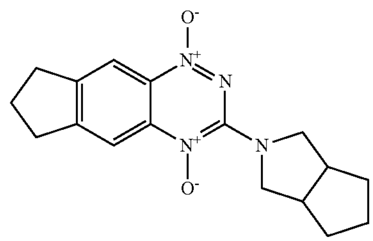 [SMILES: [O-][n+]1nc(N2CC3CCCC3C2)[n+]([O-])c2cc3c(cc21)CCC3] |
| 11 | SRI-012722 | 390.3633 | 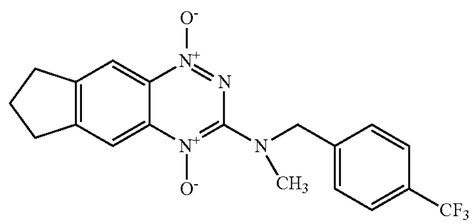 [SMILES: CN(Cc1ccc(C(F)(F)F)cc1)c1n[n+]([O-])c2cc3c(cc2[n+]1[O-])CCC3] |
| 12 | SRI-012721 | 352.392 | 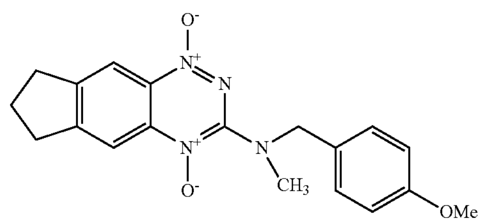 [SMILES: COc1ccc(CN(C)c2n[n+]([O-])c3cc4c(cc3[n+]2[O-])CCC4)cc1] |
| 13 | SRI-012720 | 366.3941 | 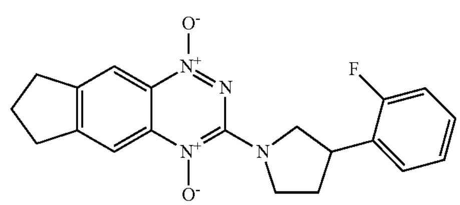 [SMILES: [O-][n+]1nc(N2CCC(c3ccccc3F)C2)[n+]([O-])c2cc3c(cc21)CCC3] |
| 14 | SRI-012621 | 340.3563 | 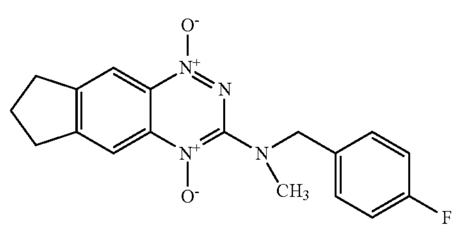 [SMILES: CN(Cc1ccc(F)cc1)c1n[n+]([O-])c2cc3c(cc2[n+]1[O-])CCC3] |
| 15 | SRI-012620 | 382.8491 | 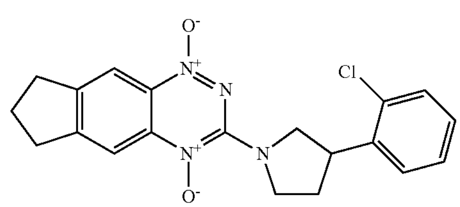 [SMILES: [O-][n+]1nc(N2CCC(c3ccccc3Cl)C2)[n+]([O-])c2cc3c(cc21)CCC3] |
| 16 | SRI-012619 | 408.4556 | 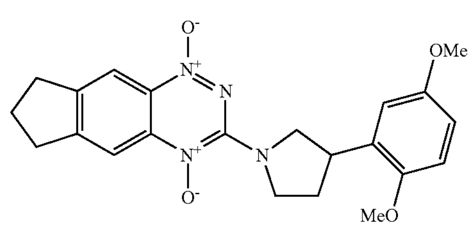 [SMILES: COc1ccc(OC)c(C2CCN(c3n[n+]([O-])c4cc5c(cc4[n+]3[O-])CCC5)C2)c1] |

TABLE E1-continued

Additional BTO Activity Data

| Cmpd # | Reference | Compound Weight | Structure |
|---|---|---|---|
| 17 | SRI-012618 | 366.3941 | (structure) |
| 18 | SRI-012616 | 408.4556 | (structure) |

| Cmpd | MIC H37Rv (ug/ml) | MBC H37Rv | MIC INH-r (ug/ml) | MIC RMP-R (ug/ml) | MIC OFX-R (ug/ml) | LORA | MP CFU red. 0.01 ug/ml | MP MTT % viable 0.01 ug/ml | MP CFU red. 0.1 ug/ml | MP MTT % viable 0.1 ug/ml | MP CFU red. 1 ug/ml | MP MTT % viable 1 ug/ml |
|---|---|---|---|---|---|---|---|---|---|---|---|---|
| 1 | 4.6 | | | | | | | | | | | |
| 2 | 1.0 | | | | | | | | | | | |
| 3 | 0.4 | | | | | | | | | | | |
| 4 | 4.6 | | | | | | | | | | | |
| 5 | 4.4 | | | | | | | | | | | |
| 6 | 0.4 | | | | | | | | | | | |
| 7 | 17.6 | | | | | | | | | | | |
| 8 | 0.7 | | | | | | | | | | | |
| 9 | 0.5 | | | | | | | | | | | |
| 10 | 0.391 | 1.56 | 0.391 | 0.098 | 0.195 | bad curve | 1.49 | 103 | 1.27 | 94 | 1.52 | 107 |
| 11 | 0.098 | 0.781 | 0.195 | 0.024 | 0.024 | 3.125 (bad curve) | 1.5 | 113 | 1.66 | 108 | 3.79 | 104 |
| 12 | 0.391 | 1.56 | 0.098 | 0.098 | 0.195 | 1.56 (bad curve) | 1.31 | 121 | 1.41 | 94 | 0 | 88 |
| 13 | 0.098 | 0.781 | 0.098 | 0.049 | 0.024 | bad curve | 1.34 | 161 | 1.04 | 123 | 2.87 | 102 |
| 14 | 0.195 | 0.781 | 0.098 | 0.049 | 0.098 | 0.391 | 0.8 | 112 | 0.79 | 82 | 3.08 | 1 |
| 15 | 0.098 | 1.56 | 0.098 | 0.098 | 0.024 | bad curve | 1.21 | 102 | 0.92 | 75 | 2.67 | 58 |
| 16 | 0.195 | 3.125 | 0.098 | 0.195 | 0.098 | bad curve | 1.72 | 122 | 1.01 | 97 | 0.35 | 108 |
| 17 | 0.098 | 0.781 | 0.049 | 0.027 | 0.049 | 0.391 | 1.16 | 104 | 0.89 | 82 | 2.87 | 69 |
| 18 | 0.391 | 1.56 | 0.195 | 0.391 | 0.049 | bad curve | 1.11 | 85 | 1.06 | 55 | 0.56 | 33 |

The term "heteroatom" as used herein generally means any atom other than carbon, hydrogen or oxygen. Preferred heteroatoms include oxygen (O), phosphorus (P), sulfur (S), nitrogen (N), silicon (S), arsenic (As), selenium (Se), and halogens, and preferred heteroatom functional groups are haloformyl, hydroxyl, aldehyde, amine, azo, carboxyl, cyanyl, thocyanyl, carbonyl, halo, hydroperoxyl, imine, aldimine, isocyanide, iscyante, nitrate, nitrile, nitrite, nitro, nitroso, phosphate, phosphono, sulfide, sulfonyl, sulfo, and sulfhydryl.

The term "alkyl," by itself or as part of another substituent, means, unless otherwise stated, a straight or branched chain, or cyclic hydrocarbon radical, or combination thereof, which is fully saturated, having the number of carbon atoms designated (i.e. C1-C8 means one to eight carbons). Examples of alkyl groups include methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like.

The term "alkenyl", by itself or as part of another substituent, means a straight or branched chain, or cyclic hydrocarbon radical, or combination thereof, which may be mono- or polyunsaturated, having the number of carbon atoms designated (i.e. C2-C8 means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl) and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e. C2-C8 means two to eight carbons) and one or more triple bonds. Examples of alkynyl groups include ethynyl, 1- and 3-propynyl, 3-butynyl and higher homologs and isomers thereof.

The term "alkylene" by itself or as part of another substituent means a divalent radical derived from alkyl, as exemplified by —CH$_2$—CH$_2$—CH$_2$—CH$_2$—. Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent means a divalent radical derived from heteroalkyl, as exemplified by —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Accordingly, a cycloalkyl group has the number of carbon atoms designated (i.e., C3-C8 means three to eight carbons) and may also have one or two double bonds. A heterocycloalkyl group consists of the number of carbon atoms designated and from one to three heteroatoms selected from the group consisting of O, N, Si and S, and wherein the nitrogen and sulfur atoms may optionally be oxidized and the nitrogen heteroatom may optionally be quaternized. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyrid-yl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" and "halogen," by themselves or as part of another substituent, mean, unless otherwise stated, a fluorine, chlorine, bromine, or iodine atom. Additionally, terms such as "haloalkyl," are meant to include alkyl substituted with halogen atoms, which can be the same or different, in a number ranging from one to (2m'+1), where m' is the total number of carbon atoms in the alkyl group. For example, the term "halo(C1-C4)alkyl" is mean to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example the term "perhalo(C1-C4)alkyl" is meant to include trifluoromethyl, pentachloroethyl, 1,1,1-trifluoro-2-bromo-2-chloroethyl and the like.

The term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like.

The term "aryl" means, unless otherwise stated, a polyunsaturated, typically aromatic, hydrocarbon substituent which can be a single ring or multiple rings (up to three rings) which are fused together or linked covalently. Non-limiting examples of aryl groups include phenyl, 1-naphthyl, 2-naphthyl, 4-biphenyl and 1,2,3,4-tetrahydronaphthalene.

The term heteroaryl," refers to aryl groups (or rings) that contain from zero to four heteroatoms selected from N, O, and S, wherein the nitrogen and sulfur atoms are optionally oxidized and the nitrogen heteroatom are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'R", —SW, halogen, —SiR'R"R'", —OC(O)R', —C(O)R', —CO$_2$R', —CONR'R", —OC(O)NR'R", —NR"C(O)R', —NR'—C(O)NR"R'", —NR'—SO$_2$NR", —NR"CO$_2$R', —NH—C(NH$_2$)=NH, —NR'C(NH$_2$)=NH, —NH—C(NH$_2$)=NR', —S(O)R', —SO$_2$R', —SO$_2$NR'R", —NR"SO$_2$R, —CN and —NO$_2$, in a number ranging from zero to three, with those groups having zero, one or two substituents being particularly preferred. R', R" and R'" each independently refer to hydrogen, unsubstituted (C1-C8) alkyl and heteroalkyl, unsubstituted aryl, aryl substituted with one to three halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF$_3$ and —CH$_2$CF$_3$).

Preferred substituents for the alkyl and heteroalkyl radicals are selected from: —OR', =O, —NR'R", —SR', halogen, —SiR'R"R'", —OC(O)R', —C(O)R', —CO$_2$R', —CONR'R", —OC(O)NR'R", —NR"C(O)R', —NR"CO$_2$R', —NR'—SO$_2$NR"R'", —S(O)R', —SO$_2$R', —SO$_2$NR'R", —NR"SO$_2$R, —CN and —NO$_2$, where R' and R" are as defined above. Further preferred substituents are selected from: —OR', =O, —NR'R", halogen, —OC(O)R', —CO$_2$R', —CONR'R", —OC(O)NR'R", —NR"C(O)R', —NR"CO$_2$R', —NR'—SO$_2$NR"R'", —SO$_2$R', —SO$_2$NR'R", —NR"SO$_2$R, —CN and —NO$_2$.

Similarly, substituents for the aryl and heteroaryl groups are varied and selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —NR"CO$_2$R', —NR'—C(O)NR"R'", —NR'—SO$_2$NR"R'", —NH—C(NH$_2$)=NH, —NR'C(NH$_2$)=NH, —NH—C(NH$_2$)=NR', —S(O)R', —SO$_2$R', —SO$_2$NR'R", —NR"SO$_2$R, —N$_3$, —CH(Ph)$_2$, perfluoro(C1-C4)alkoxy and perfluoro(C1-C4)alkyl, in a number ranging from zero to the total number of open valences on the aromatic ring system; and where R', R" and R'" are independently selected from hydrogen, (C1-C8)alkyl and heteroalkyl, unsubstituted aryl and heteroaryl, (unsubstituted aryl)-(C1-C4)alkyl and (unsubstituted aryl)oxy-(C1-C4)alkyl. When the aryl group is 1,2,3,4-tetrahydronaphthalene, it may be substituted with a substituted or unsubstituted (C3-C7)spirocycloalkyl group. The (C3-C7)spirocycloalkyl group may be substituted in the same manner as defined herein for "cycloalkyl". Typically, an aryl or heteroaryl group will have from zero to three substituents, with those groups having two or fewer substituents being preferred in the invention. In one embodiment of the invention, an aryl or heteroaryl group will be unsubstituted or monosubstituted. In another embodiment, an aryl or heteroaryl group will be unsubstituted.

Preferred substituents for aryl and heteroaryl groups are selected from: halogen, —OR', —OC(O)R', —NR'R", —SW, —R', —CN, —NO$_2$, —CO$_2$R', —CONR'R", —C(O)R', —OC(O)NR'R", —NR"C(O)R', —S(O)R', —SO$_2$R', —SO$_2$NR'R", —NR"SO$_2$R, —N$_3$, —CH(Ph)$_2$, perfluoro(C1-C4)alkoxy and perfluoro(C1-C4)alkyl, where R' and R" are as defined above. Further preferred substituents are selected from: halogen, —OR', —OC(O)R', —NR'R", —R', —CN, —NO$_2$, —CO$_2$R', —CONR'R", —NR"C(O)R', —SO$_2$R', —SO$_2$NR'R", —NR"SO$_2$R, perfluoro(C1-C4)alkoxy and perfluoro(C1-C4)alkyl.

The substituent —CO$_2$H, as used herein, includes bioisosteric replacements therefor; see, e.g., The Practice of Medicinal Chemistry; Wermuth, C. G., Ed.; Academic Press: New York, 1996; p. 203.

Two of the substituents on adjacent atoms of the aryl or heteroaryl ring may optionally be replaced with a substituent of the formula -T-C(O)—(CH$_2$)q-U-, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH2)r—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)s-X—(CH$_2$)t-, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C1-C6)alkyl. The term "pharmaceutically acceptable salts" is meant to include salts of the active compounds which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the compounds may be in a prodrug form. Prodrugs of the compounds are those compounds that undergo chemical changes under physiological conditions to provide the compounds of the invention.

Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity.

Subject compounds can exist in unsolvated forms as well as solvated forms, including hydrated forms. In general, the solvated forms are equivalent to unsolvated forms and are intended to be encompassed within the scope of the invention. Subject compounds may exist in multiple crystalline or amorphous forms. In general, all physical forms are equivalent for the uses contemplated and are intended to be within the scope of the invention.

Certain subject compounds possess asymmetric carbon atoms (optical centers) or double bonds; the racemates, diastereomers, geometric isomers and individual isomers are all intended to be encompassed within the scope of the invention.

The compositions for administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, losenges or the like in the case of solid compositions.

A wide variety of suitable formulations and delivery systems, including suitable excipients or carriers and methods for preparing administrable compositions, are known or apparent to those skilled in the art and are described in more detail in such publications as Remington: The Science and Practice of Pharmacy (Pharmaceutical Press (2012). For example, in particular embodiments the compositions are formulated or delivered in extended or controlled delivery systems, such as diffusion systems (e.g. reservoir devices, matrix devices, diffusion-controlled implants and transdermal patches) and encapsulated and matrix dissolution systems, erosion products, osmotic pump systems, ion exchange resins, etc.

In particular embodiment the amount administered is far in excess of that (200 mg) currently indicated for Parkinson's Disease, and will preferably be 0.5-10, 0.5-5, 0.5-2.5, 1-10, 1-5, 1-2.5, 2-10, or 2-5 g/day, in unit dosage forms of 0.25, 0.5, 1, 1.5, 2 or 2.5 g. The compounds can be administered by a variety of methods including, but not limited to, parenteral, topical, oral, or local administration, such as by aerosol or transdermally, for prophylactic and/or therapeutic treatment. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

Examples

Discovery and Optimization of Benzotriazine Di-N-Oxides Targeting Replicating and Non-Replicating *Mycobacterium tuberculosis*

Survey of Bioreductively-activated Antimicrobial Scaffolds. Four classes of bioreductively-activated compounds (i.e. compounds having cellular activities requiring the enzymatic transfer of electrons from reductase enzymes) were selected for screening against Mtb H37Rv. The compounds included 2- and 5-nitroimidazoles, 2-nitrofurans, quinoxaline-1,4-di-N-oxides, and BTOs (Table A). These particular classes of compounds were selected based on prior reports of known antimicrobial activities and based on availability through commercial sources or the National Cancer Institute (NCI) Developmental Therapeutics Program compound repository.[8-10] We screened the compounds for their MIC values against Mtb H37Rv strains from two sources, as well as for their MIC values against NRP Mtb in the low-oxygen recovery assay (LORA)[11] (Table 1). The primary screening was performed in two independent laboratories with different sources of the H37Rv strain to validate that the activities were not only specific for a given laboratory strain, since wide variations in lab strains of H37Rv have been reported.[12] Additionally, we tested all of the compounds for cytotoxicity against Vero cells to give a selectivity index (SI) describing the relative cytotoxicities of compounds for Mtb over a mammalian cell line.

TABLE A

Chemical structures of bioreductively-activated compounds with known antimicrobial activities.

Nitroimidazoles metronidazole etanidazole

1

TABLE A-continued

Chemical structures of bioreductively-activated compounds with known antimicrobial activities.

Nitrofurans
Quinoxaline Di-N-Oxides
Benzotriazine Di-N-Oxides

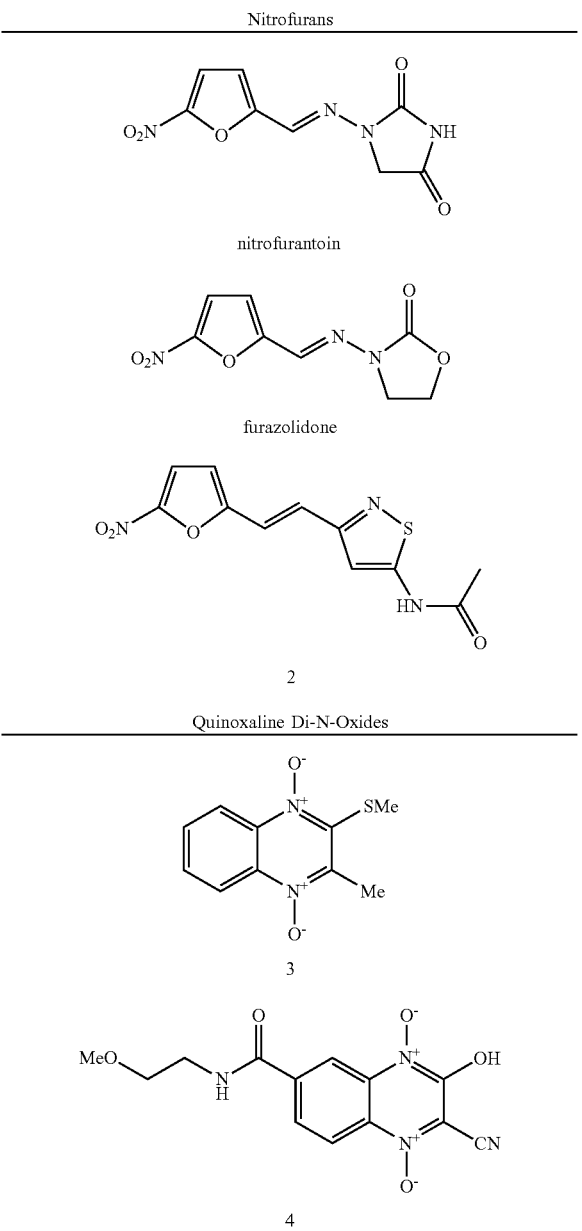
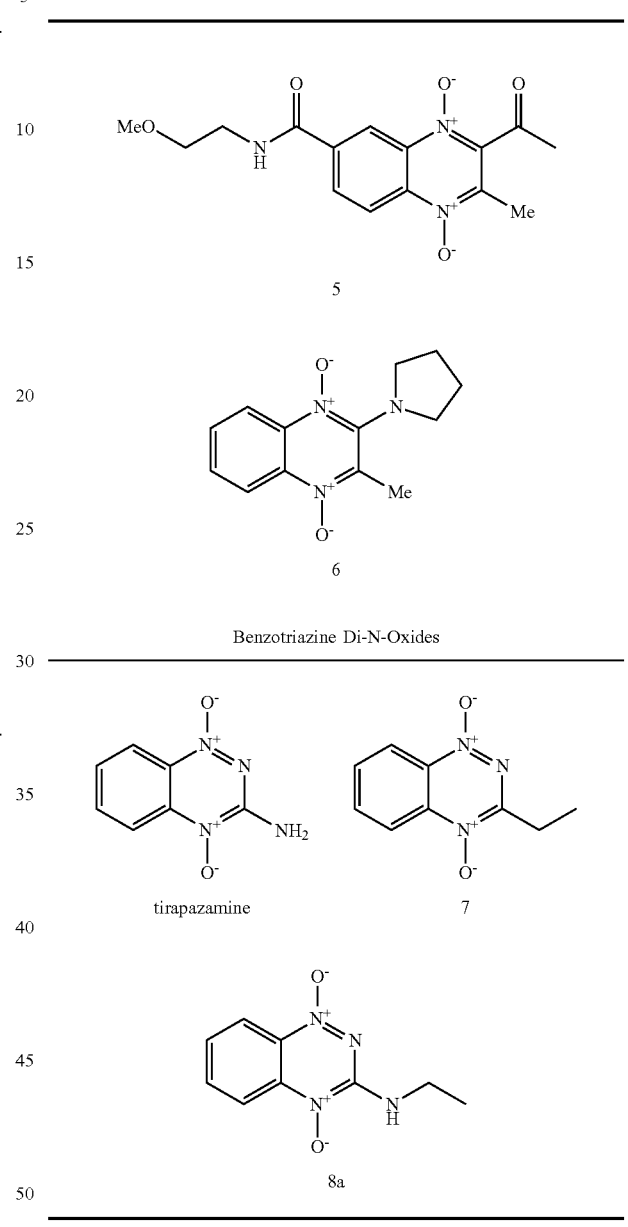

TABLE 1

Antitubercular activity of different scaffolds of bioreductively-activated antimicrobial compounds.

| Classification | Compound | LUMO (eV) | TB MIC - SRI (µg/mL) | TB MIC - ITR (µg/mL) | LORA MIC - ITR (µg/mL) | Vero Tox $CC_{50}$ (µg/mL) | SI ($CC_{50}$/MIC) |
|---|---|---|---|---|---|---|---|
| Isoniazid | INH | — | 0.060 | 0.091 | >20 | >50 | >830 |
| Rifampin | RIF | — | 0.003 | 0.041 | 2.0 | >50 | >15000 |
| Nitroimidazole | Metronidazole | −1.303 | >10 | >32 | 11 | >16 | NA |
| | Etanidazole | −1.644 | >10 | >32 | 26 | >16 | NA |
| | 1 | −1.802 | 10 | 29 | 3.3 | 16 | 1.6 |
| Nitrofurans | Nitrofurantoin | −1.801[a] | 16 | 28 | 32 | 23 | 1.1 |
| | Furazolidone | −1.652[a] | 31 | 30 | 6.5 | 19 | 0.60 |
| | 2 | −1.660[a] | 0.98 | 3.8 | 3.7 | >50 | >50 |

TABLE 1-continued

Antitubercular activity of different scaffolds of bioreductively-activated antimicrobial compounds.

| Classification | Compound | LUMO (eV) | TB MIC - SRI (μg/mL) | TB MIC - ITR (μg/mL) | LORA MIC - ITR (μg/mL) | Vero Tox $CC_{50}$ (μg/mL) | SI ($CC_{50}$/MIC) |
|---|---|---|---|---|---|---|---|
| Quinoxaline-1,4-di-N-oxides | 3 | −1.452 | 10 | 28 | 9.4 | >16 | >1.6 |
| | 4 | −2.436 | >20 | >32 | >32 | >16 | NA |
| | 5 | −1.919 | 10 | 27 | >32 | >16 | >1.6 |
| | 6 | −1.279 | >10 | >32 | >32 | >16 | NA |
| Benzotriazine-1,4-di-N-oxides | TPZ | −1.622 | 5.0 | 3.7 | 7.3 | 8.0 | 1.6 |
| | 7 | −1.703 | 5.0 | 3.7 | 0.97 | 38 | 7.6 |
| | 8a | −1.442 | 1.2 | 0.57 | 0.37 | 17 | 17 |

[a]NA = not available; ITR = Institute for Tuberculosis Research, University of Illinois at Chicago.
[b]Calculation performed for Z stereochemistry around double bond.

The data from the survey of bioreductively-activated scaffolds showed that the BTOs tested had consistent activities against both actively replicating and non-replicating Mtb. The MIC values ranged from 0.57-5 μg/mL against the actively replicating H37Rv strains and from 0.37-7.3 μg/mL in the LORA model of NRP. All of the compounds had some cytotoxicity against the Vero cells with moderate SI values. Using the results of the initial survey, we selected the anti-TB activities of the BTOs, particularly analogs of 8a, for SAR development and optimization studies.

Synthesis and Activity of N-Substituted BTOs.

The first set of new BTOs synthesized contained analogs with diverse substitutions at the 3-amine position of the ring (Scheme 1). The substitutions at this position were designed to determine how steric and electronic variations at this position affected the potency and selectivity of the compounds. The side chain modified analogs were synthesized by reacting the primary amine starting materials (Table B) with 3-chloro-benzotriazine-1-N-oxide (9). The amine adducts were then oxidized using pertrifluoroacetic acid, prepared in situ by adding trifluoroacetic anhydride (TFAA) to a stirring solution of the compound in excess hydrogen peroxide. The complete oxidation took 3-4 d with additional equivalents of TFAA added until the oxidation was complete by TLC.

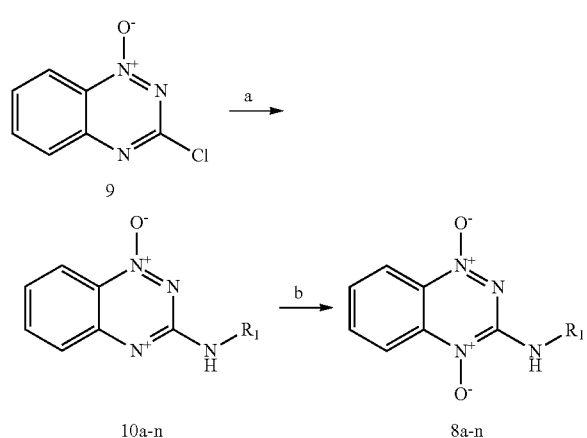

Scheme 1. Synthesis of N-alkyl 1,2,4-benzotriazine-di-N-oxides.

Reagents and conditions: (a) RNH₂ (2 eq.), TEA (2 eq.), DCM, 18 h, rt. (b) TFAA, H₂O₂, THF, 4 d.

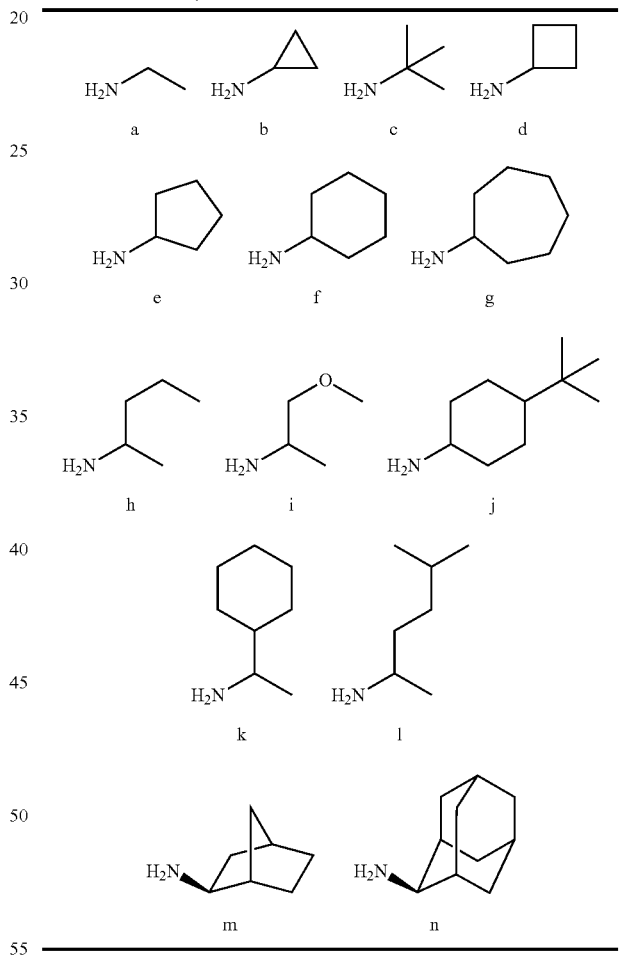

TABLE B

Amine diversity elements used for side chains on benzotriazines.

Results revealed that acyclic and cyclic alkyl groups of various sizes were tolerated at the 3-amine position, but that none of the modifications significantly increased the compounds' SIs. (Table 2) All of the compounds were active (MIC≤10 μg/mL); the most active were those with very hydrophobic side chains (8j and 8m). Incorporation of a polar ether group (8i) into the side chain resulted in a significant loss of activity, but with a comparable reduction in cytotoxicity. The overall results from this set indicated that both cyclic and acyclic substituents at this position were tolerated with the more hydrophobic groups resulting in the most potent compounds. None of the modifications in this set significantly improve the compounds' SIs, which ranged from 2.9-8.3.

TABLE 2

Antitubercular activity of side-chain-substituted BTOs.

| Com-pound | LUMO (eV) | TB MIC - SRI (μg/mL) | TB MIC - ITR (μg/mL) | LORA MIC - ITR (μg/mL) | Vero Tox CC$_{50}$ (μg/mL) | SI (CC$_{50}$/MIC) |
|---|---|---|---|---|---|---|
| 8b | −1.652 | 2.5  | 1.8  | 1.8   | 21  | 8.3  |
| 8c | −1.414 | 1.2  | 1.9  | 0.82  | 8.0 | 6.4  |
| 8d | −1.589 | 1.2  | 0.94 | 0.84  | 8.9 | 7.1  |
| 8e | −1.555 | 2.5  | 3.6  | 0.68  | 10  | 4.2  |
| 8f | −1.536 | 2.5  | 3.8  | 0.75  | 8.9 | 3.6  |
| 8g | −1.514 | 2.5  | 1.6  | 0.50  | 7.9 | 3.2  |
| 8h | −1.530 | 5.0  | 1.9  | 0.99  | 26  | 5.3  |
| 8i | −1.412 | 10.0 | 6.6  | 4.9   | >50 | >5.0 |
| 8j | −1.523 | 0.62 | 0.22 | <0.12 | 2.3 | 3.7  |
| 8k | −1.495 | 1.2  | 0.92 | 0.36  | 8.9 | 7.1  |
| 8l | −1.532 | 1.2  | 0.52 | 0.38  | 4.1 | 3.3  |
| 8m | −1.553 | 0.62 | 0.60 | 0.42  | 3.4 | 5.5  |
| 8n | −1.501 | 2.5  | 1.9  | 2.3   | 7.3 | 2.9  |

Synthesis and Activity of Ring-Substituted BTOs.

The mechanism of action for these BTOs is believed to be the bioreductive activation of the ring into a cytotoxic radical species that causes irreparable DNA damage to Mtb. Given this mechanism, the electron reduction potentials of the compounds should dictate the selectivity of the compounds for cytotoxicity to Mtb over mammalian cells. Variations to substitutions on the heterocyclic ring should significantly alter the electron reduction potentials and affect the selectivity index of the compounds.

The synthetic route for making the ring-modified BTOs began with either a substituted aniline starting material (11) or a substituted 2-nitroaniline (12) when available. (Scheme 2) The anilines were acylated, nitrated with fuming nitric acid, and then deprotected by refluxing in hydrochloric acid to give a set of 2-nitroanilines (12).[13] The 2-nitroanilines were then condensed with cyanamide in concentrated hydrochloric acid followed by treatment with base to form the 1,2,4-benzotriazine-(1N)-oxide ring. The 3-aminobenzotriazines were then converted to 3-hydroxybenzotriazines by reaction with either sodium nitrite or tert-butyl nitrite to form a diazonium intermediate, which was hydrolyzed with acid. The intermediates were chlorinated by refluxing in phosphorus oxychloride to make the 3-chlorobenzotriazine-(1N)-oxide intermediates (14a-g). Intermediates 14a-g were then reacted with a subset of the primary amine side chains (Table B; side chains a, b, d, e, f, i and m). Side chains a, b, d and f were chosen because these low molecular weight side chains yielded potent compounds without adding unnecessary additional lipophilicity.[14] Side chain i was chosen to sample a polar group at this position and m was chosen because it yielded one of the most potent compounds from the series of side-chain-substituted analogs. This set of ring-substituted BTOs was then oxidized as described in Scheme 2 to give the compounds listed in Table 3.

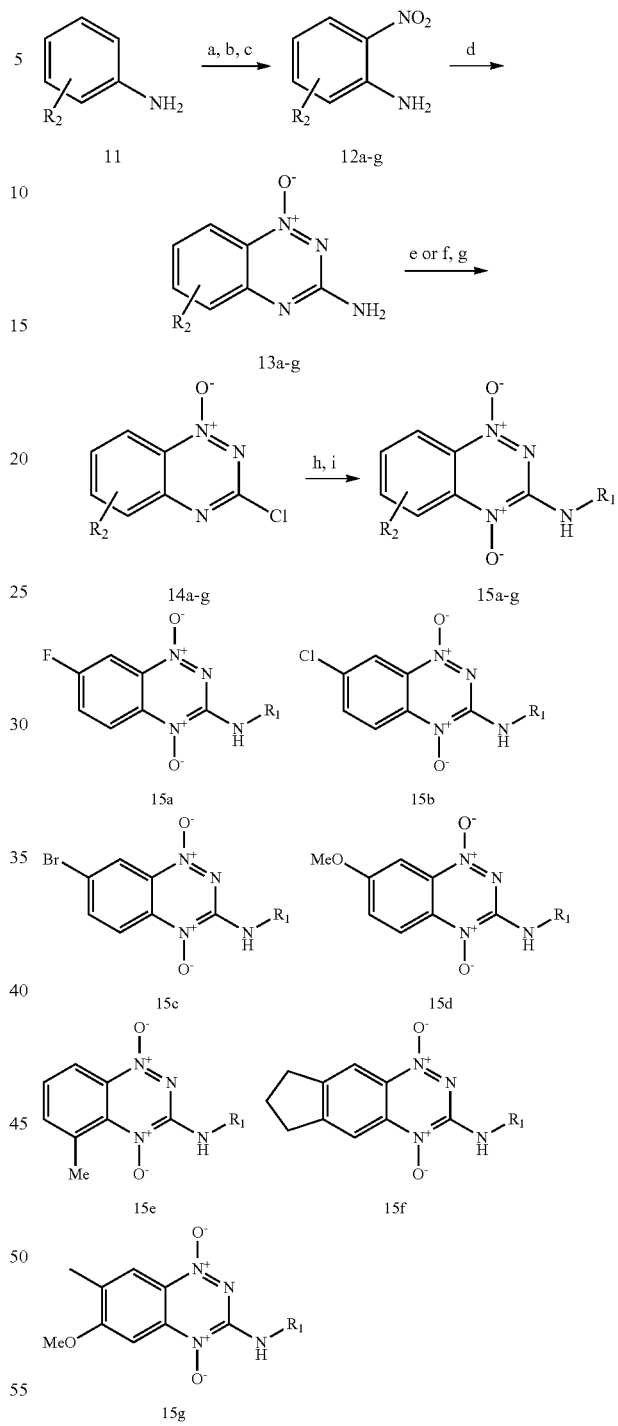

Scheme 2. Synthesis of ring substituted 1,2,4-benzotriazine-di-N-oxides.

Reagents and conditioins: (a) Ac$_2$O, TEA, DCM. (b) fHNO$_3$, Ac$_2$O, DCM. (c) HCl, reflux. (d) NCNH$_2$, conc. HCl. (e) NaNO$_2$, HCl. (f) tBuONO, tBuOH, H$_2$O. (g) POCl$_3$, reflux. (h) RNH$_2$ (2 eq.), TEA (2 eq.), DCM, 18 h, rt. (i) TFAA, H$_2$O$_2$ THF, 4 d.

All of the ring-substituted BTOs were tested for antitubercular activity and cytotoxicity (Table 3). The modifications to the ring substitutions resulted in a wide range of potencies (0.15-5 μg/mL) and cytotoxicities (<2.5-100 μg/mL). Most importantly, several of the ring substitutions led to a significant increase in SI values. The general trend observed was that electron-donating substitutions led to reduced cytotoxicities against mammalian cells. That trend fits with the hypothesis that lowering the one-electron reduction potential ($E_{1/2}$) of the compounds may be effective in increasing SI values.[15] The best compounds from this series were those with small alkyl substitutions to the benzotriazine ring, such as the 5-methyl and 6,7-cyclopentyl substitutions. These ring systems yielded compounds with SIs near 50.

TABLE 3

Antitubercular activity of ring-substituted BTOs.

| Compound | LUMO (eV) | TB MIC - SRI (μg/mL) | TB MIC - ITR (μg/mL) | LORA MIC - ITR (μg/mL) | Vero Tox $CC_{50}$ (μg/mL) | SI ($CC_{50}$/MIC) |
|---|---|---|---|---|---|---|
| 15aa | −1.704 | 0.62 | 0.35 | 0.75 | 4.6 | 7.3 |
| 15ab | −1.918 | 0.31 | 0.93 | 3.5 | 1.3 | 2.2 |
| 15ad | −1.857 | 0.31 | 0.40 | 0.88 | 1.6 | 10 |
| 15ae | −1.820 | 0.31 | 0.33 | 0.34 | 2.3 | 7.3 |
| 15af | −1.696 | 0.62 | 0.68 | 0.47 | <2.5 | <4.0 |
| 15ai | −1.716 | 5.0 | 2.0 | 1.9 | 6.3 | 1.3 |
| 15am | −1.808 | 0.31 | <0.12 | 0.21 | <2.5 | <4.0 |
| 15ba | −1.666 | 1.2 | <0.12 | 0.41 | 2.6 | 2.1 |
| 15bb | −1.870 | 0.62 | 0.21 | 0.22 | 1.3 | 2.2 |
| 15bd | −1.812 | 0.15 | <0.12 | <0.12 | 1.6 | 10 |
| 15bf | −1.655 | 0.62 | 0.94 | 0.63 | 2.6 | 4.2 |
| 15bi | −1.675 | 1.2 | 1.4 | 0.78 | 2.6 | 2.1 |
| 15bm | −1.759 | 0.15 | 0.22 | 0.23 | 1.1 | 7.3 |
| 15ca | −1.652 | 0.62 | 0.49 | 0.46 | 4.2 | 6.7 |
| 15cd | −1.793 | 0.15 | 0.46 | 0.41 | 3.8 | 24 |
| 15ce | −1.757 | 0.15 | 0.35 | 0.46 | 18 | 110 |
| 15cm | −1.749 | 0.31 | 0.36 | 0.41 | 0.80 | 2.6 |
| 15da | −1.541 | 2.5 | 15 | 16 | 16 | 6.3 |
| 15dd | −1.66 | 0.62 | 0.96 | 0.90 | 9.8 | 16 |
| 15dm | −1.629 | 0.62 | 0.97 | 1.6 | >50 | >80 |
| 15ea | −1.409 | 0.62 | 0.51 | 0.48 | 22 | 36 |
| 15ed | −1.567 | 0.31 | 0.47 | 0.43 | 22 | 70 |
| 15ee | −1.524 | 0.31 | 0.43 | 0.27 | 3.7 | 12 |
| 15fa | −1.254 | 1.2 | 0.95 | 0.83 | 36 | 29 |
| 15fd | −1.352 | 0.62 | 0.96 | 0.44 | 34 | 54 |
| 15fm | −1.244 | 1.2 | 0.93 | 0.36 | >50 | >41 |
| 15ga | −1.195 | 2.5 | 3.5 | 2.5 | >100 | >40 |
| 15gd | −1.324 | 2.5 | 5.1 | 2.9 | >50 | >20 |
| 15gm | −1.284 | 5.0 | 5.6 | 3.5 | >50 | >10 |

Synthesis and Activity of Di-N-Alkyl BTOs.

The SAR data from the side chain and ring-substituted compounds suggested that increasing the electron-donating groups around the benzotriazine ring increased the selectivity index and that modifying the alkylamine side chains increased potency, but did not considerably affect the SI. From these observations, we concluded it was desirable to synthesize new compounds with more electron-donating groups on the alkylamine side chain. In previous attempts, compounds with tri-substituted amine side chains could not be synthesized because the final oxidation reaction conditions did not produce the desired di-N-oxide product. To make these compounds, we thus explored several alternative oxidizing agents to pertrifluoroacetic acid, identifying $HOF \cdot CH_3CN$ as a sufficiently strong reagent to carry out the desired transformation, without producing significant over-oxidation side products.[16, 17] This new route allowed synthesis of a series of di-N-alky BTOs (Scheme 3). For this route, it proved preferable to oxidize the 3-chlorobenzotriazine intermediates so that the amine diversification step was the last step in the library synthesis from common intermediates 16 and 19.

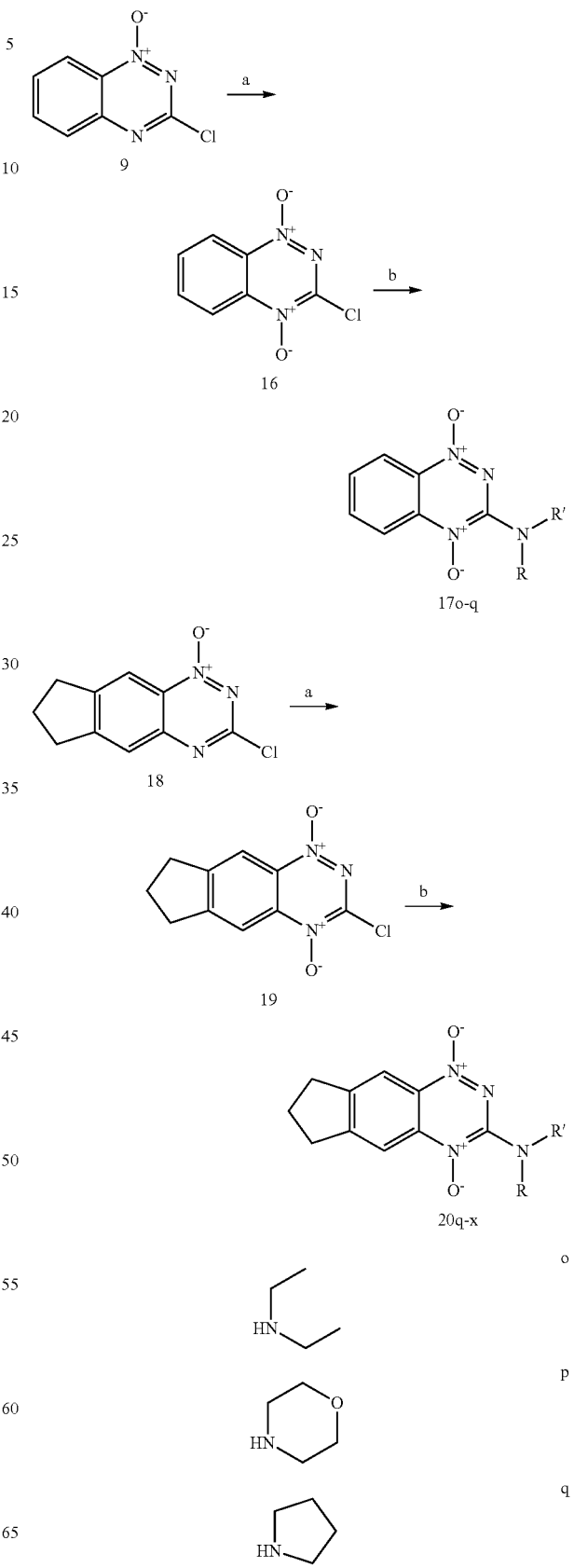

Scheme 3. Synthesis of di-N-alkyl 1,2,4-benzotriazine-di-N-oxides.

-continued

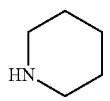
r

s

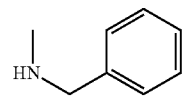
t

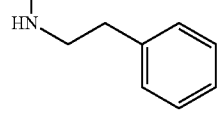
u

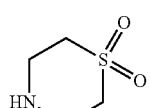
v

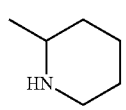
w

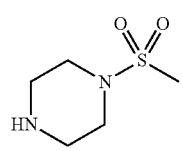
x reagents and conditions: (a) $F_2$ (g), $H_2O$, MeCN (b) $RNH_2$ (2 eq.), TEA (2 eq.), DCM, 1 h, rt.

When tested for antitubercular activity and cytotoxicity, the new di-N-alkyl BTOs were found to have increased SIs (Table 4). The antitubercular activities of the compounds were generally comparable to those of the ring-substituted analogs, but cytotoxicities against Vero cells were significantly reduced. From this set of compounds, we identified several new compounds with SIs >50. From the set of secondary amine starting materials used for this set of compounds (Scheme 3), small alkyl groups were found to have the greatest activities. The addition of polar or hydrophilic groups designed to increase solubility resulted in a significant loss of anti-TB activity.

TABLE 4

Antitubercular activity of di-N-alkyl BTOs.

| Compound | LUMO (eV) | TB MIC - SRI (µg/mL) | TB MIC - ITR (µg/mL) | LORA MIC - ITR (µg/mL) | Vero Tox $CC_{50}$ (µg/mL) | SI ($CC_{50}$/MIC) |
|---|---|---|---|---|---|---|
| 17o | −1.483 | 0.31 | 0.46 | 1.3 | 12 | 40 |
| 17p | −1.624 | 2.5 | 3.7 | 19 | 5.4 | 2.2 |
| 17q | −1.286 | 0.31 | NT | NT | 17 | 56 |
| 20q | −1.196 | 0.31 | 0.46 | 0.99 | 25 | 80 |
| 20r | −1.311 | 0.62 | 0.40 | 0.49 | 21 | 13 |
| 20s | −1.335 | 0.62 | 0.30 | 1.5 | 24 | 13 |
| 20t | −1.344 | 0.31 | 0.15 | 0.41 | 17 | 53 |
| 20u | −1.289 | 0.31 | 0.24 | 0.44 | 40 | 130 |
| 20v | −1.751 | 5.0 | 15 | 30 | 17 | 3.4 |
| 20w | −1.293 | 1.2 | 0.66 | 0.47 | >50 | >40 |
| 20x | −1.258 | 5.0 | 13 | 15 | >50 | >10 |

Activity Against Drug-Resistant Mtb Strains.

We also tested a set of the most potent and selective BTOs against a panel of single-drug resistant Mtb strains (Table 5) to determine whether or not the compounds had cross-resistance with existing TB drugs and maintained their potencies against diverse strains of Mtb. The resulting data indicated that no cross-resistance occurred and that the compounds had either equal or increased potencies against the drug-resistant strains of Mtb.

TABLE 5

MIC of BTO's against Single Drug Resistant Mtb strains.

| | | MIC Values (µg/mL) of Mtb Strains Resistant to: | | | | | |
|---|---|---|---|---|---|---|---|
| Compound | H37Rv | Streptomycin ATCC 35820 | P-aminosalicyclic acid ATCC 35821 | Isoniazid ATCC 35822 | Kanamycin ATCC 35827 | Ethionamide ATCC 35830 | Ethambutol ATCC 35837 |
| 8a | 1.2 | 1.2 | 1.2 | 1.2 | 1.2 | 1.2 | 1.2 |
| 8c | 2.5 | 1.2 | 1.2 | 2.5 | 2.5 | 1.2 | 2.5 |
| 15ea | 0.62 | 0.16 | 0.31 | 0.62 | 0.62 | 0.31 | 0.62 |
| 15fa | 1.2 | 0.63 | 1.2 | 2.5 | 1.2 | 1.2 | 1.2 |
| 15fd | 0.62 | 0.31 | 0.62 | 1.2 | 1.2 | 0.62 | 0.62 |
| 15ga | 1.2 | 1.2 | 1.2 | 1.2 | 1.2 | 1.2 | 1.2 |
| 17q | 0.31 | 0.02 | 0.62 | 0.31 | 0.31 | 0.31 | 0.31 |
| 20q | 0.62 | 0.16 | 0.31 | 0.31 | 0.63 | 0.62 | 0.62 |
| 20r | 0.62 | 0.15 | 0.31 | 0.15 | 0.31 | 0.31 | 0.31 |
| 20s | 0.62 | <0.07 | 0.15 | <0.07 | 0.31 | 0.15 | 0.31 |
| 20t | 0.31 | <0.07 | 0.07 | <0.07 | 0.15 | 0.07 | 0.15 |
| 20u | 0.31 | <0.07 | 0.15 | 0.07 | 0.15 | 0.15 | 0.31 |
| 20w | 1.2 | 0.31 | 0.62 | 0.31 | 0.62 | 0.31 | 0.62 |

Antimicrobial Spectrum of Activity for BTOs.

Given the long treatment times and complex drug combination regimens, antitubercular drugs should have a narrow spectrum of antimicrobial activity. Two BTOs, 8a and 20q, were profiled for their antimicrobial activities against a diverse panel of Gram-positive and Gram-negative bacterial pathogens (SI Table 1). Remarkably, the BTOs were highly selective in their activities for mycobacteria, with potent activity against Mtb and weaker activity against *M. smegmatis*. *M. abscessus*, which is naturally resistant to many classes of antibiotics, was resistant to both 8a and 20q.[18]

Mutagenic Potential of BTOs.

A liability in developing any bioreductively-activated antimicrobial drug is the potential for mutagenicity. Because the basis for activity of these compounds is the generation of intermediate radical species, undesirable mutagenicity poses a risk, as has been documented for many classes of bioreductive drugs, including the BTO tirapazamine (TPZ).[19,20] The most convenient methodology for assessing the potential to induce genetic damage is to use the plate incorporation method with *Salmonella typhimurium* strains TA98 and TA100, commonly known as the Ames assay. The *Salmonella* tester strains have mutations in the histidine operon, a mutation that leads to defective lipopolysaccharide (rfa), and a deletion that covers genes involved in the synthesis of biotin (bio) and in the repair of ultraviolet-induced DNA damage (uvrB).[21,22] These mutations make the strains more permeable to many molecules and increase their susceptibility to the mutagenic effects of these molecules. Given that the hypothesized mechanism of the BTO compounds is to selectively form cytotoxic radical species in bacteria over mammalian cells, a microbial mutagenicity assay is not ideal, but was used to benchmark their activities in this assay. Two BTOs, 15fa and 20q, with good potency and selectivity profiles were evaluated in the Ames assay, in both the presence and absence of an Aroclor 1254-induced rat-liver metabolic activation system containing 10% S9 (MA). Individual plate counts and their means and standard deviations, along with the condition of the background lawn, are presented in SI Table 2. There were dose-related increases in the number of revertant colonies for both 15fa and 20q with both strains TA98 and TA100 in the presence and absence of metabolic activation. In order to assess their mutagenic potential in a non-microbial system 15fa and 20q were also evaluated in the mouse lymphoma cell tk$^{+/-}$→tk$^{-/-}$ gene mutation (MOLY) assay—a routine genetic toxicology assay used to assess the mutagenic potential of compounds in mammalian cells (Table 6).[23,24] In the presence or absence of metabolic activation (S9), 15fa, at non-cytotoxic dose levels of 5, 10, 25, and 50 µg/mL showed a significant increase in mutation frequency MF. For 20q, both in the presence or absence of S9, mutation frequency did not increase at non-cytotoxic dose levels up to 100 µg/mL for 4-hr exposure and up to 10 µg/mL for 24-hr exposure in the absence of S9. In conclusion, 20q gave negative response for mutation frequency in the presence or absence of S9.

TABLE 6

Mutagenic potential of BTOs in MOLY assay. (S9 = Rat metabolic activation; Positive = A significant induction of mutation frequency; Negative = No significant induction of mutation frequency; NT = Not tested)

| Compound | Dose (µg/mL) | −S9, 4-Hr Exposure | −S9, 24-Hr Exposure | +S9, 4-Hr Exposure | +S9, 24-Hr Exposure |
|---|---|---|---|---|---|
| 15fa | 10 | Positive | NA | Positive | Positive |
|  | 25 | Positive | NA | Positive | Positive |
|  | 50 | Positive | NA | Positive | Positive |
|  | 100 | Positive | NA | Positive | Positive |

TABLE 6-continued

Mutagenic potential of BTOs in MOLY assay. (S9 = Rat metabolic activation; Positive = A significant induction of mutation frequency; Negative = No significant induction of mutation frequency; NT = Not tested)

| Compound | Dose (µg/mL) | −S9, 4-Hr Exposure | −S9, 24-Hr Exposure | +S9, 4-Hr Exposure | +S9, 24-Hr Exposure |
|---|---|---|---|---|---|
| 20q | 10 | Negative | Negative | Negative | Negative |
|  | 25 | Negative | Negative | Negative[a] | Negative |
|  | 50[a] | Negative | Negative | Negative | Negative |
|  | 100[a] | Negative | Negative | Negative | Negative |

[a]Induction of mutation frequency but slightly higher than 40 × 10$^{-6}$ net over mean solvent control, biologically considered negative.

Physiochemical Properties and Mouse Pharmacokinetics.

In order to assess the potential of BTOs as orally bioavailable therapeutics, physiochemical properties and ADME properties were profiled for 8a and 20q. The solubility of these two compounds was measured in triplicate using the shake-flask method in a 0.9% saline solution at pH 7.4. Both 8a and 20q had acceptable solubilities of 1.35 mg/mL and 0.28 mg/mL, respectively.

In order to validate BTOs as a new lead series for the treatment of TB, we also evaluated their systemic exposure in the mouse after oral administration. A single dose (100 mg/kg) of 8a and 20q were administered to mice in order to profile the pharmacokinetics for the BTOs (Table 7). Our targeted drug candidate profile is an orally administered therapeutic that requires a maximum of once-a-day dosing, and preferable 1-3 times a week dosing in order to be compatible with current first line TB drugs in a fixed dose combination tablet.[25] In order to achieve this profile, a mouse elimination half-life between 4-12 hours is being targeted in our development program. The elimination half-life was for each compound was shorter than our ideal target values, but the $T_{max}$ values indicate that they are rapidly absorbed after oral administration (FIGURE). Both compounds resulted in good exposure based on $C_{max}$ and AUC values, indicating these compounds show promise as anti-tubercular drugs.

TABLE 7

Pharmacokinetic Parameters for 8a and 20q after Oral Administration to Female Mice.

| Compound | Dose (mg/kg) | $t_{1/2}$ (hr) | $T_{max}$ (hr) | $C_{max}$ (ng/ml) | $AUC_{last}$ (hr · ng/ml) | $AUC_{inf}$ (hr · ng/ml) |
|---|---|---|---|---|---|---|
| 8a | 100 | 1.5 | 0.08 | 9540 | 6578 | 6937 |
| 20q | 100 | 1.9 | 0.25 | 9767 | 11219 | 11248 |

Our SAR indicates that hydrophobic side chains generally resulted in more potent antitubercular compounds, which was expected because compounds must pass through the hydrophobic mycobacterial cell wall to exert their activity. Increasing hydrophobicity also seemed to increase cytotoxicity to mammalian cells, presumably through increased cell permeability. Modifications to the substitutions on the BTO ring resulted in substantial changes in the selectivity of the compounds. In general, introduction of electron-withdrawing groups such as halogens, resulted in more potent compounds against Mtb (MICs of 0.15-0.31 µg/mL), but those compounds were also more cytotoxic to Vero cells. Electron-donating substitutions on the ring tended to slightly decrease potency against Mtb (MICs of 0.31-1.2 µg/mL), but substantially decreased toxicity, leading to compounds with overall improved selectivity profiles. To balance these two opposing SAR trends we selected compounds with fused tricyclic ring systems (15f), which had the most balanced potency and selectivity profiles.

The development of the oxidation chemistry to produce the di-N-alkyl BTO compounds allowed us to make compounds with 2-4 fold increases in potency against Mtb, while either maintaining or decreasing toxicity against Vero cells. All of the compounds made in this series had very good potencies (MICs of 0.31-0.62 μg/mL), except for compounds with more hydrophilic side chains containing a morpholino (17p), a sulfone (20v), or a sulfamide (20x); all those compounds demonstrated significant reductions in antitubercular activities (MICs of 2.5-5 μg/mL). Overall, the SAR trends suggested that optimal compounds should have electron-rich ring systems (lower $E_{1/2}$ values; higher LUMO energies) with hydrophobic side chains to afford compounds with maximal potencies and selectivities.

Analysis of the physiochemical properties and mouse pharmacokinetic data for 8a and 20q show that the class has good drug-like properties. The solubilities of the compounds are generally very good, most likely due to the polar nature of the N-oxide groups on the benzotriazine rings. 20q had no mutagenic activity at concentrations up to 100 μg/mL.

General Procedure for Amination/Oxidation. Method A

A primary amine (2.2 mmol) starting material was added to a stirring solution of 9 (200 mg, 1.1 mmol) dissolved in DCM (10 mL) with triethylamine (5.5 mmol) at room temperature. The solution was stirred for 24-48 hours until all of the 9 starting material was consumed as monitored by TLC (5% MeOH/DCM mobile phase). The bulky amine side chains required heating to 45° C. for complete conversion. The entire reaction was evaporated under reduced pressure to give the crude products 10a-n which were directly subjected to oxidation conditions. The crude mono-N-oxides were dissolved in a mixture of THF (8 mL) and 50% $H_2O_2$ (4 mL), then slowly treated with TFAA (3.3 mmol) while stirring at room temperature. The oxidation was monitored by TLC and additional equivalents of TFAA (3.3 mmol) were added every 12 hours until the reactions were >90% complete or no additional product was being formed. Upon completion of the reaction, the reaction was quenched with 10 mL of saturated sodium bicarbonate and extracted three times with 10 mL of chloroform. The combined organic layers were evaporated and purified by semi-preparative reversed-phase HPLC.

General Procedure for 3-Aminobenzotriazine 1-Oxides. Method B

In a 1 L 3-neck flask with mechanical stirring and a reflux condenser was placed a 2-nitroaniline (12a-h, 171 mmol), cyanamide (1.37 mol, 8 eq.) and $Et_2O$ (30 mL). The mixture was heated to 100° C. for 1 hour, then cooled to 50-55° C. Using an addition funnel concentrated HCl (72 mL) was added dropwise with mechanical stirring (CAUTION: Highly exothermic reaction.) Once the addition is complete and there no further gas evolution, the mixture was heated to 110° C. for 3 hours. The reaction was then cooled to 50° C. and a NaOH solution (7.5 M, 160 mL) was slowly added. This was then reheated to 110° C. with an oil bath for 3 hours, cooled and poured into 3 L of $H_2O$. The resulting solid was filtered off, washed with $H_2O$ and $Et_2O$, then dried under vacuum. If necessary, the product was purified by flash chromatography using silica gel with a mobile phase gradient of 0-10% MeOH in $CH_2Cl_2$.

General Procedure for 3-Chlorobenzotriazine 1-Oxides. Method C $NaNO_2$ (1.5 g, 21 mmol) was added in small portions to a stirring solution of a 3-aminobenzotriazine 1-oxide (13a-e, 7 mmol) in trifluoroacetic acid (15 mL) at room temperature. After 1 hour, 50 mL of $H_2O$ was added and the solid was filtered off and dried under vacuum. The solid was then suspended in 20 mL of $POCl_3$ and heated to reflux for 3 hours. The solution was cooled, the majority of the excess $POCl_3$ was removed by distillation and then was dissolved in $CH_2Cl_2$ (40 mL). This solution was then washed with $H_2O$ and brine, and the solvent was evaporated. The crude residue was purified by flash chromatography using silica gel and a gradient of 0-10% EtOAc in $CH_2Cl_2$.

General Procedure for 3-Chlorobenzotriazine 1-Oxides. Method D tBuONO (90%, 15 mL) and $H_2SO_4$ (1 mL) were slowly added to a stirring solution of a 3-aminobenzotriazine 1-oxide (13f-g, 9 mmol) in tBuOH (50 mL) and $H_2O$ (5 mL). After heating to 60° C. overnight the mixture added to 100 g of ice and the resulting solid was filtered off and dried under vacuum. The solid was then suspended in 20 mL of $POCl_3$ and heated to reflux for 3 hours. The solution was cooled, the majority of the excess $POCl_3$ was removed by distillation and then was dissolved in $CH_2Cl_2$ (40 mL). This solution was then washed with $H_2O$ and brine, and the solvent was evaporated. The crude residue was purified by flash chromatography using silica gel and a gradient of 0-10% EtOAc in $CH_2Cl_2$.

General Procedure for HOF.$CH_3CN$ Oxidation. Method E (CAUTION: $F_2$ and HOF.$CH_3CN$ are extremely strong oxidants and corrosive materials) 10% $F_2$ with nitrogen was slowly bubbled into 100 mL of $CH_3CN$ with 10 mL of $H_2O$ for 1 hour at −15° C. The resulting oxidant was added in one portion to a cooled (0° C.) solution of the benzotriazine 1-N-oxide (12.6 mmol) dissolved in $CH_2Cl_2$ (80 mL). The mixture was stirred for 10 minutes, then quenched with saturated $NaHCO_3$ (40 mL). The biphasic mixture was then diluted with $H_2O$ (40 mL) and extracted with $CHCl_3$ (80 mL). The organic layer was then washed with $H_2O$, brine and dried over $MgSO_4$. Solvent was evaporated and the product was purified by flash chromatography using silica gel and a mobile phase gradient of 0-10% EtOAc in $CH_2Cl_2$. Isolated yields were from 35-40% with the remainder of the mass being recovered starting material.

General Procedure for Amination of 3-Chlorobenzotriazine-1,4-Di-N-Oxides. Method F To a stirring solution of the 3-chlorobenzotriazine-1,4-di-N-oxide (2 mmol) in dimethoxyethane (12 mL) at 0° C. was added an amine (2.2 mmol) and triethylamine (2.4 mmol). The mixture was allowed to warm to room temperature and was stirred for 16 hours. After the reaction, solvent was evaporated and the crude product was purified by flash chromatography using silica gel and a mobile phase gradient of 0-10% MeOH in $CH_2Cl_2$. Typical yields were from 80-90%.

3-(ethylamino)benzo[e][1,2,4]triazine 1,4-dioxide (8a)

Synthesized from 9 by Method A. Red solid. $^1$H-NMR (DMSO-d$_6$, 400 MHz): δ 8.28 (br-s, 1H), 8.18 (d, J=8.4 Hz, 1H), 8.10 (d, J=8.5 Hz, 1H), 7.90 (t, J=7.5 Hz, 1H), 7.55 (t, J=8.6 Hz, 1H), 3.43 (m, 2H), 1.18 (t, J=7.0 Hz, 3H). MS (ESI+): m/z 207.0 ((M+H)$^+$).

3-(cyclopropylamino)benzo[e][1,2,4]triazine 1,4-dioxide (8b)

Synthesized from 9 by Method A. Red solid. $^1$H-NMR (DMSO-d$_6$, 400 MHz): δ 8.41 (d, J=2.4 Hz, 1H), 8.20 (dd, J=8.8, 0.8 Hz, 1H), 8.10 (dd, J=8.8, 0.8 Hz, 1H), 7.92 (m, 1H), 7.56 (m, 1H), 2.76 (m, 1H), 0.74 (m, 4H). MS (ESI+): m/z 219.0 ((M+H)$^+$).

3-(tert-butylamino)benzo[e][1,2,4]triazine 1,4-dioxide (8c)

Synthesized from 9 by Method A. Red solid. $^1$H-NMR (DMSO-d$_6$, 400 MHz): δ 8.31 (d, J=8.8 Hz, 1H), 8.26 (d, J=8.8 Hz, 1H), 7.83 (t, J=7.0 Hz, 1H), 7.45 (t, J=7.0 Hz, 1H), 7.19 (s, 1H), 1.55 (s, 9H). MS (ESI+): m/z 235.0 ((M+H)$^+$).

3-(cyclobutylamino)benzo[e][1,2,4]triazine 1,4-dioxide (8d)

Synthesized from 9 by Method A. Red solid. $^1$H-NMR (DMSO-d$_6$, 400 MHz): δ 8.44 (d, J=8.0 Hz, 1H), 8.17 (dd, J=8.8, 0.8 Hz, 1H), 8.10 (dd, J=8.8, 0.8 Hz, 1H), 7.91 (m, 1H), 7.54 (m, 1H), 4.33 (m, 1H), 2.24 (m, 4H), 1.67 (m, 2H). MS (ESI+): m/z 233.0 ((M+H)$^+$).

3-(cyclopentylamino)benzo[e][1,2,4]triazine 1,4-dioxide (8e)

Synthesized from 9 by Method A. Red solid. $^1$H-NMR (DMSO-d$_6$, 400 MHz): δ 8.18 (dt, J=8.8, 0.8 Hz, 1H), 8.10-8.06 (m, 2H), 7.92 (m, 1H), 7.54 (m, 1H), 4.18 (m, 1H), 1.92 (m, 2H), 1.70 (m, 4H), 1.56 (m, 2H). MS (ESI+): m/z 247.0 ((M+H)$^+$).

3-(cyclohexylamino)benzo[e][1,2,4]triazine 1,4-dioxide (8f)

Synthesized from 9 by Method A. Red solid. $^1$H-NMR (DMSO-d$_6$, 400 MHz): δ 8.16 (dd, J=8.8, 0.8 Hz, 1H), 8.08 (dt, J=8.8, 0.8 Hz, 1H), 7.95 (d, J=9.2 Hz, 1H), 7.89 (m, 1H), 7.52 (m, 1H), 3.71 (m, 1H), 1.85 (m, 2H), 1.72 (m, 2H), 1.58 (m, 1H), 1.51-1.42 (m, 2H), 1.35-1.26 (m, 2H), 1.20-1.09 (m, 1H). MS (ESI+): m/z 261.0 ((M+H)$^+$).

3-(cycloheptylamino)benzo[e][1,2,4]triazine 1,4-dioxide (8g)

Synthesized from 9 by Method A. Red solid. $^1$H-NMR (DMSO-d$_6$, 400 MHz): δ 8.18 (dt, J=8.8, 0.8 Hz, 1H), 8.09 (dt, J=8.8, 0.8 Hz, 1H), 7.96 (d, J=8.4 Hz, 1H), 7.91 (m, 1H), 7.53 (m, 1H), 3.92 (m, 1H), 1.89 (m, 2H), 1.76-1.42 (m, 10H). MS (ESI+): m/z 275.0 ((M+H)$^+$).

3-(pentan-2-ylamino)benzo[e][1,2,4]triazine 1,4-dioxide (8h)

Synthesized from 9 by Method A. Red solid. $^1$H-NMR (DMSO-d$_6$, 400 MHz): δ 8.16 (dt, J=8.8 Hz, 1H), 8.07 (dt, J=8.8, 0.4 Hz, 1H), 8.00 (d, J=9.2 Hz, 1H), 7.90 (m, 1H), 7.52 (m, 1H), 3.97 (m, 1H), 1.65 (m, 1H), 1.49 (m, 1H), 1.30 (m, 2H), 1.20 (d, J=6.4 Hz, 3H), 0.83 (t, J=7.2 Hz, 3H). MS (ESI+): m/z 249.0 ((M+H)$^+$).

3-((1-methoxybutan-2-yl)amino)benzo[e][1,2,4]triazine 1,4-dioxide (8i)

Synthesized from 9 by Method A. Red solid. $^1$H-NMR (DMSO-d$_6$, 400 MHz): δ 8.18 (dt, J=8.8, 0.8 Hz, 1H), 8.09 (dt, J=8.8, 0.8 Hz, 1H), 7.92 (m, 2H), 7.54 (m, 1H), 3.50 (dd, J=10, 6.4 Hz, 1H), 3.40 (dd, J=10, 5.2 Hz, 2H), 3.23 (s, 3H), 1.62 (m, 2H), 0.87 (m, 3H). MS (ESI+): m/z 265.0 ((M+H)$^+$).

3-((4-(tert-butyl)cyclohexyl)amino)benzo[e][1,2,4]triazine 1,4-dioxide (8j)

Synthesized from 9 by Method A. Red solid. $^1$H-NMR (DMSO-d$_6$, 400 MHz): δ 8.17 (td, J=8.4, 0.8 Hz, 1H), 8.08 (m, 1H), 7.97 (d, J=9.2 Hz, 1H), 7.91 (m, 1H), 7.57-7.50 (m, 1H), 4.06 (m, 1H), 1.94 (m, 2H), 1.75 (m, 1H), 1.58 (m, 2H), 1.14 (m, 4H), 0.83 (d, J=3.2 Hz, 9H). MS (ESI+): m/z 317.1 ((M+H)$^+$).

(R)-3-((1-cyclohexylethyl)amino)benzo[e][1,2,4]triazine 1,4-dioxide (8k)

Synthesized from 9 by Method A. Red solid. $^1$H-NMR (DMSO-d$_6$, 400 MHz): δ 8.16 (dd, J=8.8, 0.8 Hz, 1H), 8.08 (dd, J=8.8, 0.8 Hz, 1H), 7.89 (m, 2H), 7.51 (m, 1H), 3.75 (m, 1H), 1.72-1.55 (m, 6H), 1.18 (d, J=6.8 Hz, 3H), 1.12 (m, 3H), 0.92 (m, 2H). MS (ESI+): m/z 289.0 ((M+H)$^+$).

3-((5-methylhexan-2-yl)amino)benzo[e][1,2,4]triazine 1,4-dioxide (8l)

Synthesized from 9 by Method A. Red solid. $^1$H-NMR (DMSO-d$_6$, 400 MHz): δ 8.16 (dd, J=8.8, 0.8 Hz, 1H), 8.09 (dd, J=8.4, 0.4 Hz, 1H), 7.94 (d, J=9.6 Hz, 1H), 7.89 (m, 1H), 7.52 (m, 1H), 3.91 (m, 1H), 1.66 (m, 1H), 1.50 (m, 2H), 1.20 (d, J=6.8 Hz, 3H), 1.15 (m, 2H), 0.83 (dd, J=6.4, 2.0 Hz, 6H). MS (ESI+): m/z 277.0 ((M+H)$^+$).

3-((1R,2R,4S)-bicyclo[2.2.1]heptan-2-ylamino) benzo[e][1,2,4]triazine 1,4-dioxide (8m)

Synthesized from 9 by Method A. Red solid. $^1$H-NMR (DMSO-d$_6$, 400 MHz): δ 8.18 (dt, J=8.8, 0.4 Hz, 1H), 8.09 (dd, J=8.8, 0.8 Hz, 1H), 7.90 (m, 1H), 7.73 (d, J=6.8 Hz, 1H), 7.53 (m, 1H), 3.65 (m, 1H), 2.26 (m, 2H), 1.69 (m, 2H), 1.50 (m, 3H), 1.14 (m, 3H). MS (ESI+): m/z 273.0 ((M+H)$^+$).

3-((1R,3S,5r,7r)-adamantan-2-ylamino)benzo[e][1,2,4]triazine 1,4-dioxide (8n)

Synthesized from 9 by Method A. Red solid. $^1$H-NMR (DMSO-d$_6$, 400 MHz): δ 8.18 (dd, J=8.8, 0.8 Hz, 1H), 8.11 (dd, J=8.8, 1.2 Hz, 1H), 7.93 (m, 1H), 7.55 (m, 1H), 7.39 (d, J=8.4 Hz, 1H), 4.00 (m, 1H), 2.04 (m, 2H), 1.88 (m, 8H), 1.72 (br s, 2H), 1.61 (m, 2H). MS (ESI+): m/z 313.1 ((M+H)$^+$).

3-(ethylamino)-7-fluorobenzo[e][1,2,4]triazine 1,4-dioxide (15aa)

Synthesized from 4-fluoro-2-nitroaniline using Method C and Method A. Red solid. $^1$H-NMR (CDCl$_3$, 400 MHz): δ

8.26 (dd, J=4.9, 9.6; 1H), 7.92 (dd, J=1.7, 8.0; 1H), 7.57 (m, 1H), 6.94 (br-t, 1H), 3.57 (p, J=7.3, 2H), 1.29 (t, J=7.3, 3H). MS (ESI+): m/z 224.9 ((M+H)⁺).

3-(cyclopropylamino)-7-fluorobenzo[e][1,2,4]triazine 1,4-dioxide (15ab)

Synthesized from 4-fluoro-2-nitroaniline using Method C and Method A. Red solid. ¹H-NMR (DMSO-d₆, 400 MHz): δ 8.37 (br s, 1H), 8.15 (dd, J=9.6, 5.2 Hz, 1H), 7.97 (dd, J=8.4, 2.8 Hz, 1H), 7.84 (m, 1H), 2.72 (m, 1H), 0.72 (m, 4H). MS (ESI+): m/z 236.9 ((M+H)⁺).

3-(cyclobutylamino)-7-fluorobenzo[e][1,2,4]triazine 1,4-dioxide (15ad)

Synthesized from 4-fluoro-2-nitroaniline using Method C and Method A. Red solid. ¹H-NMR (DMSO-d₆, 400 MHz): δ 8.43 (d, J=8.0 Hz, 1H), 8.15 (dd, J=9.6, 5.2 Hz, 1H), 7.93 (dd, J=8.8, 2.8 Hz, 1H), 7.83 (m, 1H), 4.30 (m, 1H), 2.23 (m, 4H), 1.67 (m, 2H). MS (ESI+): m/z 250.9 ((M+H)⁺).

3-(cyclopentylamino)-7-fluorobenzo[e][1,2,4]triazine 1,4-dioxide (15ae)

Synthesized from 4-fluoro-2-nitroaniline using Method C and Method A. Red solid. ¹H-NMR (DMSO-d₆, 400 MHz): δ 8.14 (dd, J=9.6, 5.2 Hz, 1H), 7.97 (m, 1H), 7.94 (dd, J=8.4, 2.8 Hz, 1H), 7.83 (m, 1H), 4.13 (m, 1H), 1.91 (m, 2H), 1.67 (m, 4H), 1.55 (m, 2H). MS (ESI+): m/z 265.0 ((M+H)⁺).

7-fluoro-3-((1-methoxybutan-2-yl)amino)benzo[e][1,2,4]triazine 1,4-dioxide (15ag)

Synthesized from 4-fluoro-2-nitroaniline using Method C and Method A. Red solid. ¹H-NMR (DMSO-d₆, 400 MHz): δ 8.16 (dd, J=9.6, 5.2 Hz, 1H), 7.95 (dd, J=9.2, 2.8 Hz, 1H), 7.85 (m, 2H), 3.95 (m, 1H), 3.49 (dd, J=10, 6.4 Hz, 1H), 3.39 (dd, J=9.6, 5.2 Hz, 1H), 3.23 (s, 3H), 1.61 (m, 2H), 0.86 (t, J=7.2 Hz, 3H). MS (ESI+): m/z 283.0 ((M+H)⁺).

3-(cyclohexylamino)-7-fluorobenzo[e][1,2,4]triazine 1,4-dioxide (15aj)

Synthesized from 4-fluoro-2-nitroaniline using Method C and Method A. Red solid. ¹H-NMR (DMSO-d₆, 400 MHz): δ 8.14 (dd, J=9.2, 5.2 Hz, 1H), 7.95 (dd, J=8.8, 2.8 Hz, 1H), 7.91 (m, 1H), 7.83 (m, 1H), 3.69 (m, 1H), 1.84 (m, 2H), 1.71 (m, 2H), 1.58 (m, 1H), 1.51-1.41 (m, 2H), 1.35-1.25 (m, 2H), 1.12 (m, 1H). MS (ESI+): m/z 279.0 ((M+H)⁺).

3-((1R,2R,4S)-bicyclo[2.2.1]heptan-2-ylamino)-7-fluorobenzo[e][1,2,4]triazine 1,4-dioxide (15an)

Synthesized from 4-fluoro-2-nitroaniline using Method C and Method A. Red solid. ¹H-NMR (DMSO-d₆, 400 MHz): δ 8.15 (dd, J=9.6, 4.8 Hz, 1H), 7.95 (dd, J=9.2, 2.8 Hz, 1H), 7.84 (m, 1H), 7.74 (d, J=7.2 Hz, 1H), 3.61 (m, 1H), 2.28 (d, J=4.0 Hz, 1H), 2.22 (br s, 1H), 1.69 (m, 2H), 1.56 (m, 1H), 1.45 (m, 2H), 1.12 (m, 3H). MS (ESI+): m/z 291.0 ((M+H)⁺).

7-chloro-3-(ethylamino)benzo[e][1,2,4]triazine 1,4-dioxide (15ba)

Synthesized from 4-chloro-2-nitroaniline using Method C and Method A. Red solid. ¹H-NMR (DMSO-d₆, 400 MHz): δ 8.41 (t, J=6.0 Hz, 1H), 8.19 (d, J=2.4 Hz, 1H), 8.10 (d, J=9.2 Hz, 1H), 7.91 (dd, J=9.2, 2.4 Hz, 1H), 3.41 (m, 2H), 1.17 (t, J=7.2 Hz, 3H). MS (ESI+): m/z 241.0 ((M+H)⁺).

7-chloro-3-(cyclopropylamino)benzo[e][1,2,4]triazine 1,4-dioxide (15bb)

Synthesized from 4-chloro-2-nitroaniline using Method C and Method A. Red solid. ¹H-NMR (DMSO-d₆, 400 MHz): δ 8.47 (br s, 1H), 8.19 (d, J=2.0 Hz, 1H), 8.09 (d, J=9.2 Hz, 1H), 7.90 (dd, J=9.2, 2.0 Hz, 1H), 2.73 (m, 1H), 0.77-0.67 (m, 4H). MS (ESI+): m/z 253.0 ((M+H)⁺).

7-chloro-3-(cyclobutylamino)benzo[e][1,2,4]triazine 1,4-dioxide (15bd)

Synthesized from 4-chloro-2-nitroaniline using Method C and Method A. Red solid. ¹H-NMR (DMSO-d₆, 400 MHz): δ 8.55 (d, J=7.6 Hz, 1H), 8.16 (d, J=1.6 Hz, 1H), 8.09 (d, J=9.2 Hz, 1H), 7.89 (dd, J=9.2, 2.0 Hz, 1H), 4.31 (m, 1H), 2.22 (m, 4H), 1.66 (m, 2H). MS (ESI+): m/z 267.0 ((M+H)⁺).

7-chloro-3-((1-methoxybutan-2-yl)amino)benzo[e][1,2,4]triazine 1,4-dioxide (15bg)

Synthesized from 4-chloro-2-nitroaniline using Method C and Method A. Red solid. ¹H-NMR (DMSO-d₆, 400 MHz): δ 8.18 (d, J=2.4 Hz, 1H), 8.10 (d, J=9.2 Hz, 1H), 7.96 (d, J=8.8 Hz, 1H), 7.90 (dd, J=9.2, 2.4 Hz, 1H), 3.97 (m, 1H), 3.49 (dd, J=9.6, 6.4 Hz, 1H), 3.39 (m, 1H), 3.23 (m, 3H), 1.61 (m, 2H), 0.86 (t, J=7.2 Hz, 3H). MS (ESI+): m/z 299.0 ((M+H)⁺).

7-chloro-3-(cyclohexylamino)benzo[e][1,2,4]triazine 1,4-dioxide (15bj)

Synthesized from 4-chloro-2-nitroaniline using Method C and Method A. Red solid. ¹H-NMR (DMSO-d₆, 400 MHz): δ 8.17 (d, J=2.4 Hz, 1H), 8.08 (d, J=9.2 Hz, 1H), 8.02 (d, J=8.8 Hz, 1H), 7.89 (dd, J=9.2, 2.4 Hz, 1H), 3.70 (m, 1H), 1.82 (m, 2H), 1.70 (m, 2H), 1.57 (m, 1H), 1.46 (m, 2H), 1.31 (m, 2H), 1.12 (m, 1H). MS (ESI+): m/z 295.1 ((M+H)⁺).

3-((1R,2R,4S)-bicyclo[2.2.1]heptan-2-ylamino)-7-chlorobenzo[e][1,2,4]triazine 1,4-dioxide (15bn)

Synthesized from 4-chloro-2-nitroaniline using Method C and Method A. Red solid. ¹H-NMR (DMSO-d₆, 400 MHz): δ 8.18 (dd, J=2.4, 0.4 Hz, 1H), 8.08 (dd, J=9.6, 0.8 Hz, 1H), 7.90 (dd, J=9.2, 2.4 Hz, 1H), 7.85 (m, 1H), 3.62 (m, 1H), 2.28 (d, J=4.0 Hz, 1H), 2.22 (br s, 1H), 1.69 (m, 2H), 1.56 (m, 1H), 1.47 (m, 2H), 1.14 (m, 3H). MS (ESI+): m/z 307.1 ((M+H)⁺).

7-bromo-3-(ethylamino)benzo[e][1,2,4]triazine 1,4-dioxide (15ca)

Synthesized from 4-bromo-2-nitroaniline using Method C and Method A. Red solid. ¹H-NMR (DMSO-d₆, 400 MHz): δ 8.41 (t, J=6.4 Hz, 1H), 8.32 (m, 1H), 8.01 (m, 2H), 3.40 (m, 2H), 1.17 (t, J=7.2 Hz, 3H). MS (ESI+): m/z 286.9 ((M+H)⁺).

7-bromo-3-(cyclobutylamino)benzo[e][1,2,4]triazine 1,4-dioxide (15cd)

from Synthesized from 4-bromo-2-nitroaniline using Method C and Method A. Red solid. ¹H-NMR (DMSO-d₆, 400 MHz): δ 8.58 (m, 1H), 8.31 (m, 1H), 8.02 (m, 2H), 4.32 (m, 1H), 2.32 (m, 4H), 1.67 (m, 2H). MS (ESI+): m/z 312.9 ((M+H)$^+$).

7-bromo-3-(cyclopentylamino)benzo[e][1,2,4]triazine 1,4-dioxide (15ce)

Synthesized from 4-bromo-2-nitroaniline using Method C and Method A. Red solid. $^1$H-NMR (DMSO-d$_6$, 400 MHz): δ 8.32 (t, J=1.2 Hz, 1H), 8.14 (d, J=8.0 Hz, 1H), 8.01 (m, 2H), 4.16 (m, 1H), 1.92 (m, 2H), 1.70 (m, 4H), 1.56 (m, 2H). MS (ESI+): m/z 326.9 ((M+H)$^+$).

3-((1R,2R,4S)-bicyclo[2.2.1]heptan-2-ylamino)-7-bromobenzo[e][1,2,4]triazine 1,4-dioxide (15cn)

Synthesized from 4-bromo-2-nitroaniline using Method C and Method A. Red solid. $^1$H-NMR (DMSO-d$_6$, 400 MHz): δ 8.33 (t, J=1.2 Hz, 1H), 8.02 (m, 2H), 7.89 (m, 1H), 3.62 (m, 1H), 2.30 (m, 1H), 2.23 (m, 1H), 1.72 (m, 2H), 1.59-1.40 (m, 3H), 1.23-1.01 (m, 3H). MS (ESI+): m/z 352.9 ((M+H)$^+$).

3-(ethylamino)-7-methoxybenzo[e][1,2,4]triazine 1,4-dioxide (15da)

Synthesized from 4-methoxy-2-nitroaniline using Method C and Method A. Red solid. $^1$H-NMR (DMSO-d$_6$, 400 MHz): δ 8.08 (t, J=6.0 Hz, 1H), 8.04 (d, J=9.6 Hz, 1H), 7.57 (dd, J=9.6, 2.8 Hz, 1H), 7.46 (d, J=2.4 Hz, 1H), 3.90 (s, 3H), 3.38 (m, 2H), 1.17 (t, J=7.2 Hz, 3H). MS (ESI+): m/z 237.0 ((M+H)$^+$).

3-(cyclobutylamino)-7-methoxybenzo[e][1,2,4]triazine 1,4-dioxide (15dd)

Synthesized from 4-methoxy-2-nitroaniline using Method C and Method A. Red solid. $^1$H-NMR (DMSO-d$_6$, 400 MHz): δ 8.25 (d, J=8.0 Hz, 1H), 8.05 (d, J=9.6 Hz, 1H), 7.57 (dd, J=9.2, 2.8 Hz, 1H), 7.45 (d, J=2.4 Hz, 1H), 4.30 (m, 1H), 3.90 (s, 3H), 2.22 (m, 4H), 1.67 (m, 2H). MS (ESI+): m/z 263.0 ((M+H)$^+$).

3-((1R,2R,4S)-bicyclo[2.2.1]heptan-2-ylamino)-7-methoxybenzo[e][1,2,4]triazine 1,4-dioxide (15dn)

Synthesized from 4-methoxy-2-nitroaniline using Method C and Method A. Red solid. $^1$H-NMR (DMSO-d$_6$, 400 MHz): δ 8.04 (d, J=9.6 Hz, 1H), 7.56 (m, 2H), 7.46 (d, J=2.4 Hz, 1H), 3.90 (s, 3H), 3.61 (m, 1H), 2.30 (d, J=4.0 Hz, 1H), 2.23 (br s, 1H), 1.69 (m, 2H), 1.57-1.35 (m, 3H), 1.23-1.09 (m, 3H). MS (ESI+): m/z 303.0 ((M+H)$^+$).

Ethyl-(5-methyl-1,4-dioxy-benzo[1,2,4]triazin-3-yl)-amine (15ea)

Synthesized from 6-methyl-2-nitroaniline using Method C and Method A. Red solid. $^1$H-NMR (DMSO-d$_6$, 400 MHz): δ 8.34 (t, J=6.4 Hz, 1H), 8.05 (dq, J=8.8, 0.8 Hz, 1H), 7.60 (m, 1H), 7.38 (m, 1H), 3.40 (p, J=6.8 Hz, 2H), 2.95 (s, 3H), 1.18 (t, J=7.2 Hz, 3H). MS (ESI+): m/z 221.0 ((M+H)$^+$).

3-(cyclobutylamino)-5-methylbenzo[e][1,2,4]triazine 1,4-dioxide (15ed)

Synthesized from 6-methyl-2-nitroaniline using Method C and Method A. Red solid. $^1$H-NMR (DMSO-d$_6$, 400 MHz): δ 8.43 (d, J=8.0 Hz, 1H), 8.04 (d, J=8.8 Hz, 1H), 7.59 (dt, J=7.2, 1.2 Hz, 1H), 7.38 (m, 1H), 4.31 (m, 1H), 2.96 (s, 3H), 2.27-2.17 (m, 4H), 1.68 (m, 2H). MS (ESI+): m/z 247.0 ((M+H)$^+$).

3-(cyclopentylamino)-5-methylbenzo[e][1,2,4]triazine 1,4-dioxide (15ee)

Synthesized from 6-methyl-2-nitroaniline using Method C and Method A. Red solid. $^1$H-NMR (DMSO-d$_6$, 400 MHz): δ 8.05 (m, 1H), 7.95 (d, J=7.6 Hz, 1H), 7.59 (dt, J=7.2, 1.2 Hz, 1H), 7.38 (dd, J=8.8, 7.2 Hz, 1H), 4.15 (m, 1H), 2.96 (s, 3H), 1.94 (m, 2H), 1.68 (m, 4H), 1.57 (m, 2H). MS (ESI+): m/z 261.0 ((M+H)$^+$).

3-(ethylamino)-7,8-dihydro-6H-indeno[5,6-e][1,2,4]triazine 1,4-dioxide (15fa)

Synthesized from 6-nitro-2,3-dihydro-1H-inden-5-amine using Method D and Method A. Red solid. $^1$H-NMR (CDCl$_3$, 400 MHz): δ 8.11 (s, 1H), 8.07 (s, 1H), 6.94 (br-t, 1H), 3.59 (p, J=7.2, 2H), 3.09 (t, J=6.7, 2H), 3.03 (t, J=7.7, 2H), 2.20 (p, J=7.5, 2H), 1.33 (t, J=7.3, 3H). MS (ESI+): m/z 247.0 ((M+H)$^+$).

Cyclobutyl-(5,8-dioxy-2,3-dihydro-1H-5,6,8-triaza-cyclopenta[b]naphthalen-7-yl)-amine (15fd).

Synthesized from 6-nitro-2,3-dihydro-1H-inden-5-amine using Method D and Method A. Red solid. $^1$H-NMR (DMSO-d$_6$, 400 MHz): δ 8.32 (d, J=8.0 Hz, 1H), 7.99 (br s, 1H), 7.95 (br s, 1H), 4.32 (m, 1H), 3.07-2.97 (m, 4H), 2.22 (m, 4H), 2.07 (m, 2H), 1.67 (m, 2H). MS (ESI+): m/z 273.0 ((M+H)$^+$).

3-((1R,2R,4S)-bicyclo[2.2.1]heptan-2-ylamino)-7,8-dihydro-6H-indeno[5,6-e][1,2,4]triazine 1,4-dioxide (15fn)

Synthesized from 6-nitro-2,3-dihydro-1H-inden-5-amine using Method D and Method A. Red solid. $^1$H-NMR (DMSO-d$_6$, 400 MHz): δ 8.00 (br s, 1H), 7.94 (br s, 1H), 7.63 (d, J=6.8 Hz, 1H), 3.63 (m, 1H), 3.07-2.97 (m, 4H), 2.30 (d, J=4.0 Hz, 1H), 2.24 (br s, 1H), 2.07 (m, 2H), 1.70 (m, 2H), 1.57 (m, 1H), 1.49 (m, 2H), 1.15 (m, 3H). MS (ESI+): m/z 313.0 ((M+H)$^+$).

3-(ethylamino)-6-methoxy-7-methylbenzo[e][1,2,4]triazine 1,4-dioxide (15ga)

Synthesized from 5-methoxy-4-methyl-2-nitroaniline using Method D and Method A. Red solid. $^1$H-NMR (DMSO-d$_6$, 400 MHz): δ 8.17 (t, J=6.0 Hz, 1H), 7.99 (d, J=1.2 Hz, 1H), 7.33 (s, 1H), 4.00 (s, 3H), 3.42-3.36 (m, 2H), 2.26 (d, J=0.8 Hz, 3H), 1.17 (t, J=7.2 Hz, 3H). MS (ESI+): m/z 251.0 ((M+H)$^+$).

3-(cyclobutylamino)-6-methoxy-7-methylbenzo[e][1,2,4]triazine 1,4-dioxide (15gd)

Synthesized from 5-methoxy-4-methyl-2-nitroaniline using Method D and Method A. Red solid. $^1$H-NMR (DMSO-d$_6$, 400 MHz): δ 8.31 (d, J=8.4 Hz, 1H), 7.98 (m, 1H), 7.33 (s, 1H), 4.31 (m, 1H), 4.00 (s, 3H), 2.26 (d, J=0.8 Hz, 3H), 2.22 (m, 4H), 1.67 (m, 2H). MS (ESI+): m/z 277.0 ((M+H)$^+$).

3-((1R,2R,4S)-bicyclo[2.2.1]heptan-2-ylamino)-6-methoxy-7-methylbenzo[e][1,2,4]triazine 1,4-dioxide (15gn)

Synthesized from 5-methoxy-4-methyl-2-nitroaniline using Method D and Method A. Red solid. $^1$H-NMR (DMSO-d$_6$, 400 MHz): δ 8.01 (d, J=1.2 Hz, 1H), 7.60 (d, J=6.8 Hz, 1H), 7.32 (s, 1H), 4.00 (s, 3H), 3.63 (m, 1H), 2.33 (m, 1H), 2.27 (s, 3H), 2.24 (br s, 1H), 1.69 (m, 2H), 1.49 (m, 3H), 1.16 (m, 3H). MS (ESI+): m/z 317.0 ((M+H)$^+$).

3-chlorobenzo[e][1,2,4]triazine 1,4-dioxide (16)

Synthesized from 9 by Method E. Yellow solid. $^1$H-NMR (CDCl$_3$, 300 MHz): δ 8.55 (d, J=8.5, 1H), 8.48 (d, J=8.6, 1H), 8.07 (t, J=8.5 Hz, 1H), 7.90 (t, J=8.6 Hz, 1H). MS (ESI+): m/z 198.0 ((M+H)$^+$).

3-chloro-7,8-dihydro-6H-indeno[5,6-e][1,2,4]triazine 1,4-dioxide (19)

Synthesized from 18 by Method E. Yellow solid. $^1$H-NMR (CDCl$_3$, 300 MHz): δ 8.34 (s, 1H), 8.26 (s, 1H), 3.17 (q, J=7.8 Hz, 4H), 2.27 (quin, J=7.8, 2H). MS (ESI+): m/z 238.0 ((M+H)$^+$).

3-(diethylamino)benzo[e][1,2,4]triazine 1,4-dioxide (17o)

Synthesized from 16 using Method F. Red solid. $^1$H-NMR (CDCl$_3$, 300 MHz): δ 8.36 (d, J=7.4 Hz, 1H), 8.31 (d, J=7.4 Hz, 1H), 7.85 (t, J=7.4 Hz, 1H), 7.54 (t, J=7.4 Hz, 1H), 3.81 (q, J=6.9 Hz, 4H), 1.32 (t, J=7.0 Hz, 6H). (ESI+): m/z 235.0 ((M+H)$^+$).

3-morpholinobenzo[e][1,2,4]triazine 1,4-dioxide (17p)

Synthesized from 16 using Method F. Red solid. $^1$H-NMR (CDCl$_3$, 300 MHz): δ 8.39 (d, J=8.7 Hz, 1H), 8.35 (d, J=9.6 Hz, 1H), 7.90 (t, J=7.0 Hz, 1H), 7.65 (t, J=7.0, 1H), 3.91 (m, 4H), 3.87 (m, 4H). (ESI+): m/z 249.1 ((M+H)$^+$).

3-(pyrrolidin-1-yl)benzo[e][1,2,4]triazine 1,4-dioxide (17q)

Synthesized from 16 using Method F. Red solid. $^1$H-NMR (CDCl$_3$, 300 MHz): δ 8.31 (d, J=5.8 Hz, 2H), 7.84 (t, J=5.8, 1H), 7.49 (t, J=5.8 Hz, 1H), 4.04 (m, 4H), 1.98 (m, 4H). (ESI+): m/z 233.0 ((M+H)$^+$).

3-(pyrrolidin-1-yl)-7,8-dihydro-6H-indeno[5,6-e][1,2,4]triazine 1,4-dioxide (20q)

Synthesized from 19 using Method F. Red solid. $^1$H-NMR (CDCl$_3$, 300 MHz): δ 8.11 (s, 1H), 8.10 (s, 1H), 4.03 (t, J=6.6, 4H), 3.07 (t, J=7.3 Hz, 2H), 3.04 (t, J=7.5 Hz, 2H), 2.19 (quin, J=7.4 Hz, 2H), 1.98 (m, 4H). MS (ESI+): m/z 273.0 ((M+H)$^+$).

3-(piperidin-1-yl)-7,8-dihydro-6H-indeno[5,6-e][1,2,4]triazine 1,4-dioxide (20r)

Synthesized from 19 using Method F. Red solid. $^1$H-NMR (CDCl$_3$, 300 MHz): δ 8.15 (s, 1H), 8.11 (s, 1H), 3.76 (m, 4H), 3.05 (m, 4H), 2.18 (quintet, J=7.5 Hz, 2H), 1.69 (m, 6H). MS (ESI+): m/z 287.0 ((M+H)$^+$).

3-(dimethylamino)-7,8-dihydro-6H-indeno[5,6-e][1,2,4]triazine 1,4-dioxide (20s)

Synthesized from 19 using Method F. Red solid. $^1$H-NMR (CDCl$_3$, 300 MHz): δ 8.15 (s, 1H), 8.10 (s, 1H), 3.31 (s, 6H), 3.05 (quint, J=6.9 Hz, 4H), 2.15 (quint, J=7.3 Hz, 2H). MS (ESI+): m/z 247.0 ((M+H)$^+$).

3-(benzyl(methyl)amino)-7,8-dihydro-6H-indeno[5,6-e][1,2,4]triazine 1,4-dioxide (20t)

Synthesized from 19 using Method F. Red solid. $^1$H-NMR (CDCl$_3$, 300 MHz): δ 8.24 (s, 1H), 8.16 (s, 1H), 7.25-7.35 (m, 5H), 5.1 (s, 2H), 3.17 (s, 3H), 3.12 (quint, J=7.6 Hz, 4H), 2.21 (quint, J=7.6 Hz, 2H). MS (ESI+): m/z 323.0 ((M+H)$^+$).

3-(methyl(phenethyl)amino)-7,8-dihydro-6H-indeno[5,6-e][1,2,4]triazine 1,4-dioxide (20u)

Synthesized from 19 using Method F. Red solid. $^1$H-NMR (CDCl$_3$, 300 MHz): δ 8.09 (s, 1H), 8.05 (s, 1H), 7.21 (d, J=7.4 Hz, 2H), 7.11 (t, J=5.2 Hz, 2H), 7.00 (t, J=7.4 Hz, 1H), 4.16 (t, J=7.6 Hz, 2H), 3.24 (s, 3H), 2.97-3.11 (m, 6H), 2.18 (quint, J=7.6 Hz, 2H). MS (ESI+): m/z 337.0 ((M+H)$^+$).

3-(thiomorpholinosulfone-1-yl)-7,8-dihydro-6H-indeno[5,6-e][1,2,4]triazine 1,4-dioxide (20v)

Synthesized from 19 using Method F. Red solid. $^1$H-NMR (CDCl$_3$, 300 MHz): δ 8.17 (s, 1H), 8.14 (s, 1H), 4.35 (m, 2H), 3.26 (m, 2H), 3.12 (m, 2H), 2.23 (quint, J=7.4 Hz, 2H). MS (ESI+): m/z 337.0 ((M+H)$^+$).

3-(2-methylpiperidin-1-yl)-7,8-dihydro-6H-indeno[5,6-e][1,2,4]triazine 1,4-dioxide (20w)

Synthesized from 19 using Method F. Red solid. $^1$H-NMR (CDCl$_3$, 300 MHz): δ 8.16 (s, 1H), 8.12 (s, 1H), 4.18 (t, J=7.0 Hz, 1H), 4.18 (d, J=13.2 Hz, 1H), 3.32 (m, 1H), 3.03 (m, 4H), 2.16 (quint, J=7.3 Hz, 2H), 1.92 (m, 1H), 1.62 (m, 6H), 1.33 (d, J=7.0 Hz, 3H). MS (ESI+): m/z 301.0 ((M+H)$^+$).

3-(4-(methylsulfonyl)piperazin-1-yl)-7,8-dihydro-6H-indeno[5,6-e][1,2,4]triazine 1,4-dioxide (20x)

Synthesized from 19 using Method F. Red solid. $^1$H-NMR (CDCl$_3$, 300 MHz): δ 8.15 (s, 1H), 8.12 (s, 1H), 3.95 (m, 4H), 3.42 (m, 4H), 3.07 (quint, J=5.9 Hz, 4H), 2.79 (s, 3H), 2.17 (quint, J=7.7 Hz, 2H). MS (ESI+): m/z 366.0 ((M+H)$^+$).

Calculation of LUMO Energies:

Molecular orbital energy calculations were performed using the semiempirical quantum chemistry program MOPAC2009.[52] The calculation was performed with the Neglect of Diatomic Differential Overlap (NDDO) approximation method with the PM6 parameterization. The geometries of all compounds were optimized using the default Eigenvector Following routine until a self-consistent field was achieved. The energies of the LUMO for each molecule is approximated by the eigenvalues (in eV) of the appropriate orbital generated using the EIGEN and VECTORS keywords.

Bacterial Strains, Growth Conditions, and Chemicals:

Mtb strains were obtained from the American Type Culture Collection (ATCC, VA) and Colorado State University (CSU) and cultured in roller bottles (Corning Inc) using Middlebrook 7H9 broth (Difco Laboratories) supplemented with 0.2% glycerol, 0.05% Tween-80, and 10% albumin-dextrose-catalase (Difco Laboratories). Middlebrook 7H10 agar (Difco Laboratories), supplemented with 0.2% glycerol and 10% oleic acid-albumin-dextrose-catalase (Difco Laboratories), was used to visualize colonies. Mtb H37Rv was grown in 7H9 broth at 37'C to the mid-log phase. The antibiotics and resazurin were purchased from Sigma (St. Louis, Mo.) and resuspended according to the manufacturer's instructions. Experiments performed at the Institute for Tuberculosis Research at the University of Illinois Chicago (TB MIC-ITR) were performed according to published methods.[11,53]

Determination of Antibiotic Susceptibility:

To determine the MIC of compounds against Mtb, the resazurin-based microplate assay was performed. Briefly, the compounds were resuspended in DMSO and tested in a range from 10-0.08 mg/L following a two-fold dilution scheme. After addition of the bacterial cells ~$10^5$ colony forming unit (CFU)/mL, the 96 well plates were incubated at 37'C for 5 d. The addition of 0.05 mL of 0.1% resazurin followed, with additional incubation for 2 d at 37'C. Fluorescence was measured using a Fluoroskan Ascent or Victor 3 microplate fluorimeter (Thermo Scientific, USA) with an excitation of 530 nm and emission of 590 nm. Wells containing compounds only were used to detect autofluorescence of compounds. The lowest drug concentration that inhibited ≥90% growth was considered to be the MIC. In addition to the fluorescence readouts, all of the MIC values are also scored by visual inspection for confirmation of the MIC value. A two-fold variation in MIC was considered to be within the error range of the assay. The final concentration of DMSO in all wells was 0.625%. These data are presented in Tables 1-5.

Antimicrobial Activity Against NRP Mtb Cells:

The antimicrobial activity of various compounds against NRP Mtb cells was determined as described previously using LORA.[7] Briefly, Mtb H37Rv cells were suspended in Middlebrook 7H12 broth and sonicated for 15 s. Cultures were diluted to obtain an $OD_{570}$ of 0.03-0.05 and 3000-7000 relative light units (RLU) per 100 µL. Two-fold serial dilutions of antimicrobial agents were prepared in a volume of 100 µL in black 96-well microtiter plates, and 100 µL of the cell suspension was added. The microplate cultures were placed under anaerobic conditions ($O_2$<0.16%) using an Anoxomat Model WS-8080 (MART Microbiology) using three cycles of evacuation and filling with a mixture of 10% $H_2$, 5% $CO_2$, and the balance $N_2$. An anaerobic indicator strip was placed inside the chamber to visually confirm the removal of $O_2$. Plates are incubated at 37'C for 10 d and then transferred to an ambient gaseous condition (5% $CO_2$-enriched air) incubator for a 28-h "recovery". On day 11 (after the 28-h aerobic recovery), 100 µL culture were transferred to white 96-well microtiter plates for determination of luminescence. The MIC was defined as the lowest drug concentration effecting an inhibition of ~90% relative to drug-free controls.

Cytotoxicity Against Vero Cells.

The compounds were tested for cytotoxicity against Vero cells using the Cell Titer-Glo Luminescent Cell Viability Assay (Promega). The Vero cells (Vero ATCC CCL-81) were grown and maintained in minimal essential medium (MEM)+0.25% fetal bovine serum (FBS). Compound dilutions were done in accordance with Clinical and Laboratory Standards Institute (CLSI) guidelines in 96-well plates. Each well contained 5 µL of compound and 95 µL of host Vero cells at a concentration of ~$5 \times 10^4$ cells/mL. Plates were incubated for 72 h at 37'C+5% $CO_2$, followed by equilibration of the plate to room temperature for ~30 min. Addition of the Cell Titer-Glo reagent followed, with mixing the contents for 2 min on an orbital shaker to induce cell lysis and further incubation at room temperature for 10 min to stabilize the luminescent signal. The plates were read and the luminescence was recorded. Each test plate contained a set of controls including media only (for background subtraction) and 0.625% DMSO controls (for calculating the percent viability for all test wells). In addition, each test plate contained an ATP standard curve, which was used to calculate the ATP units in each test well. The toxicity was defined as the concentration at which host cells are 50% viable ($IC_{50}$).

Mouse Lymphoma Cell tk+/−→tk−/− Gene Mutation Assay.

Experiments were conducted using a standard procedure for evaluating mutagenic potential.[23,24] The details on cell line, experimental procedures and data interpretaion have been previously published.[54] The following endpoints were evaluated in cells following exposure to 15fa and 20q: cell growth during expression periods, relative suspension growth, relative total growth, relative cloning efficiency, mutation frequency, and numbers of small (≤0.6 mm in diameter) colonies from trifluorothymidine-resistant ($TFT^r$) cells.

Solubility Assays.

Compounds were ground into a fine powders using a mortar and pestle and added to a 25 mL glass Erlenmeyer flask with 5 mL of a 0.9% saline solution at pH 7.4. Approximately 20 mg of compound was added to each flask to ensure saturation. The flasks were then vigorously stirred using a magnetic stir bar at 25° C. for 48 hours. The samples were then filtered through a Whatman PVDF membrane (0.45 µm pore size) syringe filter. The concentration of compound in the supernatant was then measured using HPLC quantitation at the maximum absorption wavelength for each compound. The integration was then fit to a standard curve generated for each compound ($R^2$ values>0.99) to determine the equilibrium solubility for each compound.

Pharmacokinetic Studies in Female CD1 Mice.

All pharmacokinetic studies were performed in accordance with SRI International's animal care policies in an AAALAC and OLAW accredited facility. The procedure for the pharmacokinetics studies followed a previously described method.[55] Briefly, the plasma pharmacokinetics of selected BTO derivatives were determined in female CD1 mice after administration of a single dose (100 mg/kg) by oral gavage. Blood was collected from three mice per time point at 5, 15, 30, and 60 min and 2, 4, 6, 8, and 24 h after dose administration. Means and standard deviations were calculated for the plasma drug concentrations at each time point. Pharmacokinetic analysis was performed using non compartmental methods (WinNonlin® Professional, Version 5.2, Pharsight Corp, Mountain View, Calif.). The following parameters were calculated: time to maximum plasma concentration ($T_{max}$), maximum plasma concentration ($C_{max}$), maximum plasma concentration extrapoloated to time 0 ($C_0$), area under the plasma concentration-time curve to the last time point ($AUC_{last}$) and to infinity ($AUC_{inf}$).

Abbreviations Used:

ATCC, American Type Culture Collection: BTO, 1,2,4-benzotriazine di-N-oxides; $CC_{50}$, cytotoxicity concentration; $CDCl_3$, deuterated chloroform; $CD_3OD$, deuterated methanol; CFU, colony forming unit; CLSI, Clinical and Laboratory Standards Institute; CSI. Colorado State University; DOTS, direct observed therapy short-course; $E_{1/2}$, one electron reduction potential; ES-MS, electrospray mass spectra; FBS, fetal bovine serum; LC-MS-MS, liquid chromatograph tandem mass spectrometer; LCQ, liquid chromatography quadrupole; LORA, low-oxygen recovery assay; MDR-TB, multidrug-resistant TB; MEM, minimal essential medium; MLM, mouse liver microsome; MOLY, mouse lymphoma cell mutation assay; Mtb, *Mycobacterium tuberculosis*; NRP, nonreplicating persistence; RLU, relative light unit; SD, standard deviation; SI, selectivity index; TB, tuberculosis; TFAA, trifluoroacetic anhydride; TI, therapeutic index; TPZ, tirapazamine; XDR, extensively drug-resistant.

SUPPORTING INFORMATION TABLE 1

Spectrum of antimicrobial activity for BTOs.

| Bacterial strains | Source | 8a (µg/mL) | 20q (µg/mL) |
|---|---|---|---|
| Mtb H37Rv | CSU | 1.2 | 0.31 |
| *Mycobacterium smegmatis* | ATCC 10143 | 5.0 | 2.5 |
| *Mycobacterium abscessus* | ATCC 19977 | >32 | >32 |
| *Klebsiella pneumoniae* | ATCC 700721 | >32 | >32 |
| *Klebsiella pneumoniae* | ATCC 43816 | >32 | >32 |
| *Enterobacter aerogenes* | ATCC 29751 | >32 | >32 |
| *Enterobacter aerogenes* | SRI Collection | >32 | >32 |
| *Escherichia coli* | BAA 201 | 16 | >32 |
| *Escherichia coli* | ATCC 25922 | 16 | >32 |
| *Acinetobacter baumannii* | BAA 1605 | >32 | >32 |
| *Acinetobacter baumannii* | ATCC 17978 | 32 | >32 |
| *Staphylococcus aureus* | ATCC 29213 | >32 | >32 |
| *Staphylococcus aureus* HA-MRSA | NRS 382 | 16-32 | >32 |

SUPPORTING INFORMATION TABLE 1-continued

Spectrum of antimicrobial activity for BTOs.

| Bacterial strains | Source | 8a (µg/mL) | 20q (µg/mL) |
|---|---|---|---|
| *Enterococcus fecalis* | ATCC 29212 | 16 | >32 |
| *Enterococcus fecalis* | ATCC 51575 | 32 | >32 |
| *Escherichia coli* pKM101 | SRI Collection | 32 | >32 |
| *Salmonella typhimurium* -Hisg46 | SRI Collection | >32 | >32 |
| *Salmonella choleraesuis* | ATCC 13311 | 32 | >32 |
| *Pseudomonas aeruginosa* | ATCC 27853 | >32 | >32 |
| *Enterococcus faecium* | ATCC 19434 | >32 | >32 |
| *Moraxella catarrhalis* | ATCC 25238 | 32 | 10 |

Experimental Method for the *Salmonella*/Microsome Plate Incorporation Assay (Ames Screen).

Experimental compounds were screened for microbial mutagenicity activity using the plate incorporation method with *Salmonella typhimurium* tester strains TA98 and TA100, in the presence and absence of an Aroclor 1254-induced rat-liver metabolic activation system containing 10% S9 (MA). The presence of the appropriate genetic characteristics was verified for the strains used in this study. Stock solutions were made by dissolving each test sample in dimethyl sulfoxide (DMSO) at 5 mg/ml. These initial stock concentrations were then serially diluted to achieve dose formulations of 100, 50, 10, 5, 1, 0.5, and 0.1 µg/plate (dosing volume 100 µl). Test plates were compared with the control plates for their revertant count and for the condition of the background bacterial lawn. A test article was considered a mutagen when the mean number of revertant colonies on the test plates exceeds the mean solvent control counts by at least a two-fold margin. Dose relatedness was also taken into account when evaluating a mutagenic response. Cytotoxicity was estimated by several parameters: a substantial decrease in the number of revertant colonies on the test plates, clearing or absence of the background bacterial lawn growth, formation of pinpoint nonrevertant colonies, or complete absence of bacterial growth.

SUPPORTING INFORMATION TABLE 2

Evaluation of 15fa and 20q in the *Salmonella*/Microsome Plate Incorporation Assay (Ames Screen).

| Strain | Compound | Dose level per plate | Mean revertants per plate | Standard Deviation | Ratio treated/ solvent | Individual revertant colony counts |
|---|---|---|---|---|---|---|
| Data for Positive Controls: | | | | | | |
| Without metabolic activation | | | | | | |
| TA98 | 2NF | 5 µg | 1230.7 | 94.6 | 48.3 | 1247, 1129, 1316 |
| TA100 | SA | 5 µg | 1620.0 | 32.6 | 10.0 | 1589, 1617, 1654 |
| TA98 | DMSO | — | 20.3 | 3.8 | 0.8 | 16, 22, 23 |
| TA100 | DMSO | — | 157.3 | 10.2 | 1.0 | 169, 153, 150 |
| With metabolic activation (10% S9) | | | | | | |
| TA98 | 2AN (10% S9) | 2µg | 543.3 | 20.0 | 15.3 | 528, 536, 566 |
| TA100 | 2AN (10% S9) | 2µg | 490.0 | 37.7 | 2.9 | 532, 459, 479 |
| TA98 | DMSO (+S9) | — | 30.3 | 10.4 | 0.9 | 27, 22, 42 |
| TA100 | DMSO (+S9) | — | 174.7 | 21.5 | 1.0 | 158, 167, 199 |

Key to Positive Controls
2NF 2-Nitrofluorene
SA Sodium Azide
2AN (10% S9) 2-Aminoanthracene (10% S9)
DMSO (+S9) Dimethyl Sulfoxide +S9
Key to Plate Postfix Codes SUPPORTING INFORMATION TABLE 2-continued Evaluation of 15fa and 20q in the Salmonella/Microsome Plate Incorporation Assay (Ames Screen).

Data for 15fa:

| Strain | Compound | Dose level per plate | Mean revertants per plate | Standard Deviation | Ratio treated/ solvent | Individual revertant colony counts |
|---|---|---|---|---|---|---|
| | Without metabolic activation |||||||
| TA98 | 15fa | 0.1 µg | 21.0 | 1.4 | 0.8 | 22, 20 |
| | 15fa | 0.5 µg | 19.0 | 4.2 | 0.7 | 22, 16 |
| | 15fa | 1 µg | 26.0 | 5.7 | 1.0 | 30, 22 |
| | 15fa | 5 µg | 47.0 | 2.8 | 1.8 | 45, 49 |
| | 15fa | 10 µg | 45.0 | 5.7 | 1.8 | 41, 49 |
| | 15fa | 50 µg | 141.0 | 45.3 | 5.5 | 109, 173 N |
| | 15fa | 100 µg | 215.5 | 9.2 | 8.5 | 222 N, 209 N |
| | DMSO | | 25.5 | 0.7 | | 26, 25 |
| | Untreated Control | | 22.2 | 5.5 | | 26, 27, 14, 25, 19 |
| TA100 | 15fa | 0.1 µg | 127.0 | 5.7 | 0.8 | 131, 123 |
| | 15fa | 0.5 µg | 137.0 | 1.4 | 0.8 | 138, 136 |
| | 15fa | 1 µg | 150.5 | 2.1 | 0.9 | 152, 149 |
| | 15fa | 5 µg | 259.0 | 8.5 | 1.6 | 253, 265 |
| | 15fa | 10 µg | 299.5 | 33.2 | 1.8 | 323, 276 |
| | 15fa | 50 µg | 913.5 | 99.7 | 5.6 | 984, 843 N |
| | 15fa | 100 µg | 1268.0 | 271.5 | 7.8 | 1076 N, 1460 N |
| | DMSO | | 162.5 | 44.5 | | 194, 131 |
| | Untreated Control | | 165.2 | 12.0 | | 149, 172, 177, 172, 156 |
| | With metabolic activation (10% S9) |||||||
| TA98 | 15fa | 0.1 µg | 35.5 | 6.4 | 1.0 | 31, 40 |
| | 15fa | 0.5 µg | 36.0 | 1.4 | 1.0 | 37, 35 |
| | 15fa | 1 µg | 30.5 | 0.7 | 0.9 | 31, 30 |
| | 15fa | 5 µg | 37.0 | 0.0 | 1.0 | 37, 37 |
| | 15fa | 10 µg | 52.0 | 0.0 | 1.5 | 52, 52 |
| | 15fa | 50 µg | 142.5 | 6.4 | 4.0 | 138, 147 N |
| | 15fa | 100 µg | 345.0 | 39.6 | 9.7 | 317 N, 373 N |
| | DMSO | | 35.5 | 2.1 | | 37, 34 |
| TA100 | 15fa | 0.1 µg | 145.5 | 0.7 | 0.9 | 146, 145 |
| | 15fa | 0.5 µg | 148.5 | 4.9 | 0.9 | 152, 145 |
| | 15fa | 1 µg | 185.0 | 8.5 | 1.1 | 179, 191 |
| | 15fa | 5 µg | 207.0 | 12.7 | 1.2 | 198, 216 |
| | 15fa | 10 µg | 298.5 | 37.5 | 1.8 | 272, 325 |
| | 15fa | 50 µg | 854.5 | 30.4 | 5.1 | 833, 876 N |
| | 15fa | 100 µg | 1450.0 | 12.7 | 8.6 | 1441 N, 1459 N |
| | DMSO | | 168.5 | 12.0 | | 160, 177 |

Key to Positive Controls
Key to Plate Postfix Codes
N Normal background lawn

Data for 20q:

| Strain | Compound | Dose level per plate | Mean revertants per plate | Standard Deviation | Ratio treated/ solvent | Individual revertant colony counts |
|---|---|---|---|---|---|---|
| | Without metabolic activation |||||||
| TA98 | 20q | 0.1 µg | 33.0 | 2.8 | 1.0 | 31 N, 35 N |
| | 20q | 0.5 µg | 50.5 | 2.1 | 1.6 | 52 N, 49 N |
| | 20q | 1 µg | 85.0 | 5.7 | 2.7 | 81 N, 89 N |
| | 20q | 5 µg | 241.0 | 18.4 | 7.5 | 228 N, 254 N |
| | 20q | 10 µg | 378.5 | 89.8 | 11.8 | 315 N, 442 N |
| | 20q | 50 µg | 797.0 | 4.2 | 24.9 | 800 N, 794 N |
| | 20q | 100 µg | 1133.0 | 32.5 | 35.4 | 1110 N, 1156 N |
| | DMSO | | 32.0 | 5.2 | | 38, 29, 29 |
| | Untreated Control | | 33.6 | 8.0 | | 42, 37, 38, 29, 22 |
| TA100 | 20q | 0.1 µg | 173.0 | 8.5 | 1.2 | 179 N, 167 N |
| | 20q | 0.5 µg | 155.0 | 14.1 | 1.0 | 165 N, 145 N |
| | 20q | 1 µg | 206.0 | 4.2 | 1.4 | 203 N, 209 N |
| | 20q | 5 µg | 303.0 | 25.5 | 2.0 | 321 N, 285 N |
| | 20q | 10 µg | 392.0 | 36.8 | 2.6 | 366 N, 418 N |
| | 20q | 50 µg | 1033.5 | 50.2 | 7.0 | 998 N, 1069 N |
| | 20q | 100 µg | 1468.0 | 29.7 | 9.9 | 1489 N, 1447 N |
| | DMSO | | 148.3 | 8.1 | | 154, 139, 152 |
| | Untreated Control | | 143.4 | 12.6 | | 153, 146, 123, 154, 141 |
| | With metabolic activation (10% S-9) |||||||
| TA98 | 20q | 0.1 µg | 39.5 | 3.5 | 1.4 | 42 N, 37 N |
| | 20q | 0.5 µg | 30.0 | 0.0 | 1.1 | 30 N, 30 N |

SUPPORTING INFORMATION TABLE 2-continued

Evaluation of 15fa and 20q in the Salmonella/Microsome Plate Incorporation Assay (Ames Screen).

|       | 20q  | 1 µg    | 47.5   | 2.1  | 1.7  | 46 N, 49 N     |
|-------|------|---------|--------|------|------|----------------|
|       | 20q  | 5 µg    | 124.0  | 9.9  | 4.5  | 117 N, 131 N   |
|       | 20q  | 10 µg   | 266.5  | 10.6 | 9.8  | 259 N, 274 N   |
|       | 20q  | 50 µg   | 988.0  | 4.2  | 36.1 | 991 N, 985 N   |
|       | 20q  | 100 µg  | 1566.0 | 82.0 | 57.3 | 1508 N, 1624 N |
|       | DMSO |         | 27.3   | 6.1  |      | 34, 22, 26     |
| TA100 | 20q  | 0.1 µg  | 171.5  | 31.8 | 1.1  | 149 N, 194 N   |
|       | 20q  | 0.5 µg  | 204.0  | 1.4  | 1.3  | 205 N, 203 N   |
|       | 20q  | 1 µg    | 180.5  | 4.9  | 1.1  | 177 N, 184 N   |
|       | 20q  | 5 µg    | 267.0  | 8.5  | 1.7  | 273 N, 261 N   |
|       | 20q  | 10 µg   | 291.5  | 14.8 | 1.8  | 302 N, 281 N   |
|       | 20q  | 50 µg   | 700.5  | 23.3 | 4.4  | 684 N, 717 N   |
|       | 20q  | 100 µg  | 916.0  | 21.2 | 5.8  | 901 N, 931 N   |
|       | DMSO |         | 157.7  | 4.5  |      | 162, 158, 153  |

Key to Positive Controls
DMSO Dimethyl Sulfoxide
Key to Plate Postfix Codes
N Normal background lawn

REFERENCES

1. Gillespie, S. H. Evolution of drug resistance in *Mycobacterium tuberculosis*: clinical and molecular perspective. *Antimicrob Agents Chemother* 2002, 46, 267-274.
2. Wayne, L. G.; Hayes, L. G. An in vitro model for sequential study of shiftdown of *Mycobacterium tuberculosis* through two stages of nonreplicating persistence. *Infect. Immun.* 1996, 64, 2062-2069.
3. Stover, C. K.; Warrener, P.; VanDevanter, D. R.; Sherman, D. R.; Arain, T. M.; Langhorne, M. H.; Anderson, S. W.; Towell, J. A.; Yuan, Y.; McMurray, D. N.; Kreiswirth, B. N.; Barry, C. E.; Baker, W. R. A small-molecule nitroimidazopyran drug candidate for the treatment of tuberculosis. *Nature* 2000, 405, 962-966.
4. Matsumoto, M.; Hashizume, H.; Tomishige, T.; Kawasaki, M.; Tsubouchi, H.; Sasaki, H.; Shimokawa, Y.; Komatsu, M. OPC-67683, a nitro-dihydro-imidazooxazole derivative with promising action against tuberculosis in vitro and in mice. *PLoS Med* 2006, 3, e466.
5. Diacon, A. H.; Dawson, R.; Hanekom, M.; Narunsky, K.; Venter, A.; Hittel, N.; Geiter, L. J.; Wells, C. D.; Paccaly, A. J.; Donald, P. R. Early bactericidal activity of delamanid (OPC-67683) in smear-positive pulmonary tuberculosis patients. *Int. J. Tuberc. Lung Dis.* 2011, 15, 949-954.
6. Diacon, A. H.; Dawson, R.; Hanekom, M.; Narunsky, K.; Maritz, S. J.; Venter, A.; Donald, P. R.; van Niekerk, C.; Whitney, K.; Rouse, D. J.; Laurenzi, M. W.; Ginsberg, A. M.; Spigelman, M. K. Early bactericidal activity and pharmacokinetics of PA-824 in smear-positive tuberculosis patients. *Antimicrob Agents Chemother* 2010, 54, 3402-3407.
7. Tasneen, R.; Li, S. Y.; Peloquin, C. A.; Taylor, D.; Williams, K. N.; Andries, K.; Mdluli, K. E.; Nuermberger, E. L. Sterilizing Activity of Novel TMC207- and PA-824-Containing Regimens in a Murine Model of Tuberculosis. *Antimicrob Agents Chemother* 2011, 55, 5485-5492.
8. Compounds I-6 were obtained through the National Institute of Health, National Cancer Institute, Developmental Therapeutics Program; 2003.
9. Dirlam, J. P.; Presslitz, J. E.; Williams, B. J. Synthesis and antibacterial activity of some 3-[(alkylthio)methyl]quinoxaline 1-oxide derivatives. *J Med Chem* 1983, 26, 1122-1126.
10. Kelson, A. B.; McNamara, J. P.; Pandey, A.; Ryan, K. J.; Dorie, M. J.; McAfee, P. A.; Menke, D. R.; Brown, J. M.; Tracy, M. 1,2,4-Benzotriazine 1,4-dioxides. An important class of hypoxic cytotoxins with antitumor activity. *Anticancer Drug Des* 1998, 13, 575-592.
11. Cho, S. H.; Warit, S.; Wan, B.; Hwang, C. H.; Pauli, G. F.; Franzblau, S. G. Low-oxygen-recovery assay for high-throughput screening of compounds against nonreplicating *Mycobacterium tuberculosis*. *Antimicrob Agents Chemother* 2007, 51, 1380-1385.
12. Ioerger, T. R.; Feng, Y.; Ganesula, K.; Chen, X.; Dobos, K. M.; Fortune, S.; Jacobs, W. R., Jr.; Mizrahi, V.; Parish, T.; Rubin, E.; Sassetti, C.; Sacchettini, J. C. Variation among genome sequences of H37Rv strains of *Mycobacterium tuberculosis* from multiple laboratories. *J Bacteriol* 2010, 192, 3645-3653.
13. Hay, M. P.; Hicks, K. O.; Pchalek, K.; Lee, H. H.; Blaser, A.; Pruijn, F. B.; Anderson, R. F.; Shinde, S. S.; Wilson, W. R.; Denny, W. A. Tricyclic [1,2,4]triazine 1,4-dioxides as hypoxia selective cytotoxins. *J Med Chem* 2008, 51, 6853-6865.
14. Perola, E. An Analysis of the Binding Efficiencies of Drugs and Their Leads in Successful Drug Discovery Programs. *Journal of Medicinal Chemistry* 2010, 53, 2986-2997.
15. Boshoff, H. I.; Barry, C. E., 3rd. Tuberculosis—metabolism and respiration in the absence of growth. *Nat Rev Microbiol* 2005, 3, 70-80.
16. Carmeli, M.; Rozen, S. A new efficient route for the formation of quinoxaline N-oxides and N,N'-dioxides using HOF.CH3CN. *J Org Chem* 2006, 71, 5761-5765.
17. Carmeli, M.; Rozen, S. Oxidation of azides by the $HOF.CH_3CN$: a novel synthesis of nitro compounds. *J Org Chem* 2006, 71, 4585-4589.
18. Medjahed, H.; Gaillard, J.-L.; Reyrat, J.-M. *Mycobacterium abscessus*: a new player in the mycobacterial field. *Trends in Microbiology* 2010, 18, 117-123.
19. Olive, P. L.; Banath, J. P.; Durand, R. E. Detection of subpopulations resistant to DNA-damaging agents in spheroids and murine tumours. *Mutat Res* 1997, 375, 157-165.
20. Voogd, C. E. On the mutagenicity of nitroimidazoles. *Mutat Res* 1981, 86, 243-277.
21. Ames, B. N.; McCann, J.; Yamasaki, E. Methods for detecting carcinogens and mutagens with the *Salmonella/mammalian-microsome* mutagenicity test. *Mutat Res* 1975, 31, 347-364.

22. McCann, J.; Spingarn, N. E.; Kobori, J.; Ames, B. N. Detection of carcinogens as mutagens: bacterial tester strains with R factor plasmids. *Proc Natl Acad Sci USA* 1975, 72, 979-983.

23. Clive, D.; Johnson, K. O.; Spector, J. F.; Batson, A. G.; Brown, M. M. Validation and characterization of the L5178Y/TK+/− mouse lymphoma mutagen assay system. *Mutat Res* 1979, 59, 61-108.

24. Moore, M. M.; Honma, M.; Clements, J.; Harrington-Brock, K.; Awogi, T.; Bolcsfoldi, G.; Cifone, M.; Collard, D.; Fellows, M.; Flanders, K.; Gollapudi, B.; Jenkinson, P.; Kirby, P.; Kirchner, S.; Kraycer, J.; McEnaney, S.; Muster, W.; Myhr, B.; O'Donovan, M.; Oliver, J.; Ouldelhkim, M. C.; Pant, K.; Preston, R.; Riach, C.; San, R.; Shimada, H.; Stankowski, L. F., Jr. Mouse lymphoma thymidine kinase gene mutation assay: follow-up International Workshop on Genotoxicity Test Procedures, New Orleans, La., April 2000. *Environ Mol Mutagen* 2002, 40, 292-299.

25. Koul, A.; Arnoult, E.; Lounis, N.; Guillemont, J.; Andries, K. The challenge of new drug discovery for tuberculosis. *Nature* 2011, 469, 483-490.

26. Cheman, J.; Choi, J.; Nayyar, A.; Manjunatha, U. H.; Mukherjee, T.; Lee, Y. S.; Boshoff, H. I.; Singh, R.; Ha, Y. H.; Goodwin, M.; Lakshminarayana, S. B.; Niyomrattanakit, P.; Jiricek, J.; Ravindran, S.; Dick, T.; Keller, T. H.; Dartois, V.; Barry, C. E., 3rd. Structure-activity relationships of antitubercular nitroimidazoles. 3. Exploration of the linker and lipophilic tail of ((s)-2-nitro-6,7-dihydro-5H-imidazo[2,1-b][1,3]oxazin-6-yl)-(4-trifluoromethoxybenzyl)amine (6-amino PA-824). *J Med Chem* 2011, 54, 5639-5659.

27. Kim, P.; Kang, S.; Boshoff, H. I.; Jiricek, J.; Collins, M.; Singh, R.; Manjunatha, U. H.; Niyomrattanakit, P.; Zhang, L.; Goodwin, M.; Dick, T.; Keller, T. H.; Dowd, C. S.; Barry, C. E., 3rd. Structure-activity relationships of antitubercular nitroimidazoles. 2. Determinants of aerobic activity and quantitative structure-activity relationships. *J Med Chem* 2009, 52, 1329-1344.

28. Kim, P.; Zhang, L.; Manjunatha, U. H.; Singh, R.; Patel, S.; Jiricek, J.; Keller, T. H.; Boshoff, H. I.; Barry, C. E., 3rd; Dowd, C. S. Structure-activity relationships of antitubercular nitroimidazoles. 1. Structural features associated with aerobic and anaerobic activities of 4- and 5-nitroimidazoles. *J Med Chem* 2009, 52, 1317-1328.

29. Palmer, B. D.; Thompson, A. M.; Sutherland, H. S.; Blaser, A.; Kmentova, I.; Franzblau, S. G.; Wan, B.; Wang, Y.; Ma, Z.; Denny, W. A. Synthesis and structure-activity studies of biphenyl analogues of the tuberculosis drug (6S)-2-nitro-6-{[4-(trifluoromethoxy)benzyl]oxy}-6,7-dihydro-5H-imidazo[2,1-b][1,3]oxazine (PA-824). *J Med Chem* 2010, 53, 282-294.

30. Thompson, A. M.; Blaser, A.; Anderson, R. F.; Shinde, S. S.; Franzblau, S. G.; Ma, Z.; Denny, W. A.; Palmer, B. D. Synthesis, reduction potentials, and antitubercular activity of ring A/B analogues of the bioreductive drug (6S)-2-nitro-6-{[4-(trifluoromethoxy)benzyl]oxy}-6,7-dihydro-5H-imidazo[2,1-b][1,3]oxazine (PA-824). *J Med Chem* 2009, 52, 637-645.

31. Hodgkiss, R. J. Use of 2-nitroimidazoles as bioreductive markers for tumour hypoxia. *Anticancer Drug Des* 1998, 13, 687-702.

32. Hevener, K. E.; Ball, D. M.; Buolamwini, J. K.; Lee, R. E. Quantitative structure-activity relationship studies on nitrofuranyl anti-tubercular agents. *Bioorg Med Chem* 2008, 16, 8042-8053.

33. Tangallapally, R. P.; Yendapally, R.; Lee, R. E.; Lenaerts, A. J. Synthesis and evaluation of cyclic secondary amine substituted phenyl and benzyl nitrofuranyl amides as novel antituberculosis agents. *J Med Chem* 2005, 48, 8261-8269.

34. Ancizu, S.; Moreno, E.; Solano, B.; Villar, R.; Burguete, A.; Torres, E.; Perez-Silanes, S.; Aldana, I.; Monge, A. New 3-methylquinoxaline-2-carboxamide 1,4-di-N-oxide derivatives as anti-*Mycobacterium tuberculosis* agents. *Bioorg Med Chem* 2010, 18, 2713-2719.

35. Moreno, E.; Ancizu, S.; Perez-Silanes, S.; Torres, E.; Aldana, I.; Monge, A. Synthesis and antimycobacterial activity of new quinoxaline-2-carboxamide 1,4-di-N-oxide derivatives. *Eur J Med Chem* 2010, 45, 4418-4426.

36. Ortega, M. A.; Sainz, Y.; Montoya, M. E.; Lopez De Cerain, A.; Monge, A. Synthesis and antituberculosis activity of new 2-quinoxalinecarbonitrile 1,4-di-N-oxides. *Pharmazie* 1999, 54, 24-25.

37. Torres, E.; Moreno, E.; Ancizu, S.; Barea, C.; Galiano, S.; Aldana, I.; Monge, A.; Perez-Silanes, S, New 1,4-di-N-oxide-quinoxaline-2-ylmethylene isonicotinic acid hydrazide derivatives as anti-*Mycobacterium tuberculosis* agents. *Bioorg Med Chem Lett* 2011, 21, 3699-3703.

38. Vicente, E.; Perez-Silanes, S.; Lima, L. M.; Ancizu, S.; Burguete, A.; Solano, B.; Villar, R.; Aldana, I.; Monge, A. Selective activity against *Mycobacterium tuberculosis* of new quinoxaline 1,4-di-N-oxides. *Bioorg Med Chem* 2009, 17, 385-389.

39. Villar, R.; Vicente, E.; Solano, B.; Perez-Silanes, S.; Aldana, I.; Maddry, J. A.; Lenaerts, A. J.; Franzblau, S. G.; Cho, S. H.; Monge, A.; Goldman, R. C. In vitro and in vivo antimycobacterial activities of ketone and amide derivatives of quinoxaline 1,4-di-N-oxide. *J Antimicrob Chemother* 2008, 62, 547-554.

40. Vicente, E.; Villar, R.; Perez-Silanes, S.; Aldana, I.; Goldman, R. C.; Monge, A. Quinoxaline 1,4-di-N-oxide and the potential for treating tuberculosis. *Infect Disord Drug Targets* 2011, 11, 196-204.

41. Zeman, E. M.; Baker, M. A.; Lemmon, M. J.; Pearson, C. I.; Adams, J. A.; Brown, J. M.; Lee, W. W.; Tracy, M. Structure-activity relationships for benzotriazine di-N-oxides. *Int J Radiat Oncol Biol Phys* 1989, 16, 977-981.

42. Zeman, E. M.; Brown, J. M.; Lemmon, M. J.; Hirst, V. K.; Lee, W. W. SR-4233: a new bioreductive agent with high selective toxicity for hypoxic mammalian cells. *Int J Radiat Oncol Biol Phys* 1986, 12, 1239-1242.

43. Brown, J. M. Tumor hypoxia, drug resistance, and metastases. *J Natl Cancer Inst* 1990, 82, 338-339.

44. Brown, J. M. The hypoxic cell: a target for selective cancer therapy—eighteenth Bruce F. Cain Memorial Award lecture. *Cancer Res* 1999, 59, 5863-5870.

45. Delahoussaye, Y. M.; Evans, J. W.; Brown, J. M. Metabolism of tirapazamine by multiple reductases in the nucleus. *Biochem Pharmacol* 2001, 62, 1201-1209.

46. Fitzsimmons, S. A.; Lewis, A. D.; Riley, R. J.; Workman, P. Reduction of 3-amino-1,2,4-benzotriazine-1,4-di-N-oxide (tirapazamine, WIN 59075, SR 4233) to a DNA-damaging species: a direct role for NADPH:cytochrome P450 oxidoreductase. *Carcinogenesis* 1994, 15, 1503-1510.

47. Riley, R. J.; Hemingway, S. A.; Graham, M. A.; Workman, P. Initial characterization of the major mouse cytochrome P450 enzymes involved in the reductive metabolism of the hypoxic cytotoxin 3-amino-1,2,4-benzotriazine-1,4-di-N-oxide (tirapazamine, SR 4233, WIN 59075). *Biochem Pharmacol* 1993, 45, 1065-1077.

48. Wang, J.; Biedermann, K. A.; Wolf, C. R.; Brown, J. M. Metabolism of the bioreductive cytotoxin SR 4233 by tumour cells: enzymatic studies. *Br J Cancer* 1993, 67, 321-325.
49. Anderson, R. F.; Shinde, S. S.; Hay, M. P.; Gamage, S. A.; Denny, W. A. Activation of 3-amino-1,2,4-benzotriazine 1,4-dioxide antitumor agents to oxidizing species following their one-electron reduction. *J Am Chem Soc* 2003, 125, 748-756.
50. Maccoll, A. Reduction Potentials of Conjugated Systems. *Nature* 1949, 163, 178-179.
51. Purwantini, E.; Gillis, T. P.; Daniels, L. Presence of F420-dependent glucose-6-phosphate dehydrogenase in *Mycobacterium* and *Nocardia* species, but absence from *Streptomyces* and *Corynebacterium* species and methanogenic Archaea. *FEMS Microbiol. Lett.* 1997, 146, 129-134.
52. Stewart, J. J. P. MOPAC2009, Stewart Computational Chemistry, Colorado Springs, Colo., USA, 2008.
53. Collins, L.; Franzblau, S. G. Microplate alamar blue assay versus BACTEC 460 system for high-throughput screening of compounds against *Mycobacterium tuberculosis* and *Mycobacterium avium*. *Antimicrob Agents Chemother* 1997, 41, 1004-1009.
54. Doppalapudi, R. S.; Riccio, E. S.; Rausch, L. L.; Shimon, J. A.; Lee, P. S.; Mortelmans, K. E.; Kapetanovic, I. M.; Crowell, J. A.; Mirsalis, J. C. Evaluation of chemopreventive agents for genotoxic activity. *Mutat Res* 2007, 629, 148-160.
55. Ray, S.; Madrid, P. B.; Catz, P.; LeValley, S. E.; Furniss, M. J.; Rausch, L. L.; Guy, R. K.; DeRisi, J. L.; Iyer, L. V.; Green, C. E.; Mirsalis, J. C. Development of a new generation of 4-aminoquinoline antimalarial compounds using predictive pharmacokinetic and toxicology models. *J Med Chem* 2010, 53, 3685-3695.

What is claimed is:

1. A compound of having a structure selected from the following table:

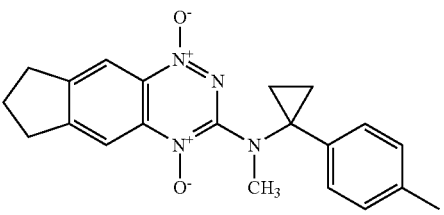 [SMILES: Cc1ccc(C2(N(C)c3n[n+]([O-])c4cc5c(cc4[n+]3[O-])CCC5)CC2)cc1]

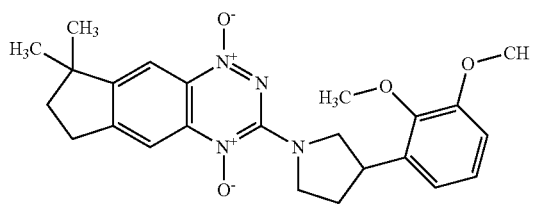

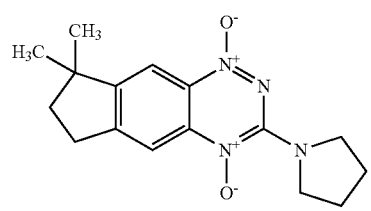 [SMILES: CC1(C)CCc2cc3c(cc21)[n+]([O-])nc(N1CCCC1)[n+]3[O-]]

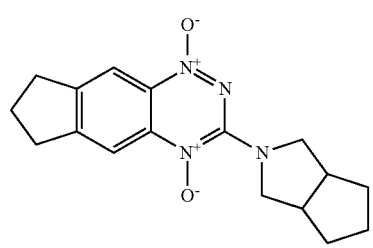 [SMILES: [O-][n+]1nc(N2CC3CCCC3C2)[n+]([O-])c2cc3c(cc21)CCC3]

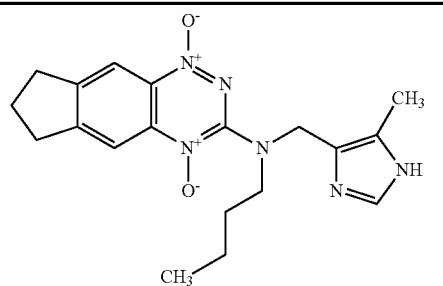

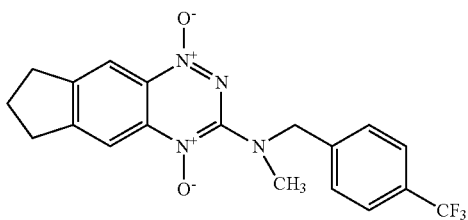 [SMILES: CN(Cc1ccc(C(F)(F)F)cc1)c1n[n+]([O-])c2cc3c(cc2[n+]1[O-])CCC3]

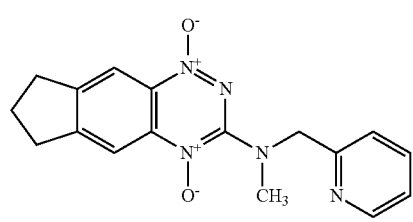

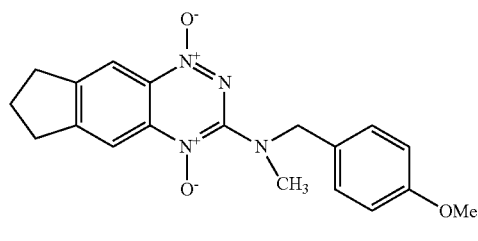 [SMILES: COc1ccc(CN(C)c2n[n+]([O-])c3cc4c(cc3[n+]2[O-])CCC4)cc1]

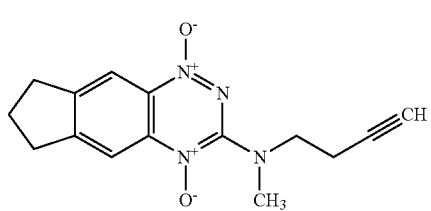

-continued
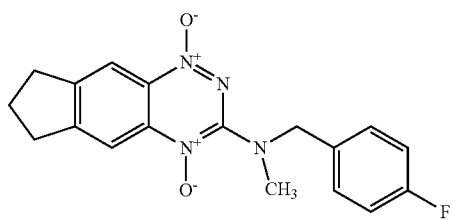 [SMILES: CN(Cc1ccc(F)cc1)c1n[n+]([O-])c2cc3c(cc2[n+]1[O-])CCC3]
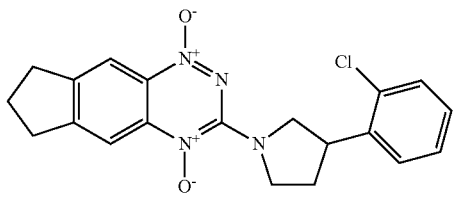 [SMILES: [O-][n+]1nc(N2CCC(c3ccccc3Cl)C2)[n+]([O-])c2cc3c(cc21)CCC3]
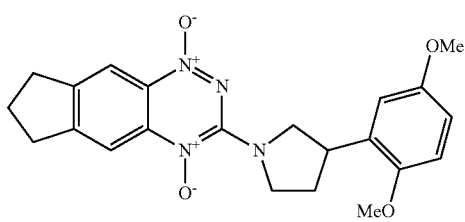 [SMILES: COc1ccc(OC)c(C2CCN(c3n[n+]([O-])c4cc5c(cc4[n+]3[O-])CCC5)C2)c1]
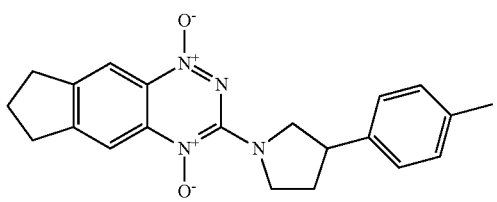 [SMILES: Cc1ccc(C2CCN(c3n[n+]([O-])c4cc5c(cc4[n+]3[O-])CCC5)C2)cc1]
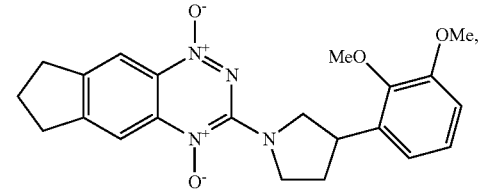 [SMILES: COc1cccc(C2CCN(c3n[n+]([O-])c4cc5c(cc4[n+]3[O-])CCC5)C2)c1OC]
or a pharmaceutically acceptable salt or stereoisomer thereof.
2. The compound of claim 1 that is:
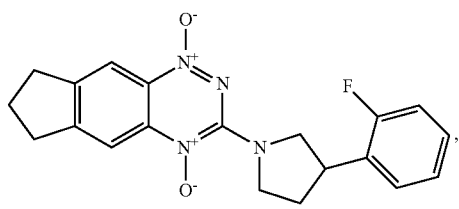 [SMILES: [O-][n+]1nc(N2CCC(c3ccccc3F)C2)[n+]([O-])c2cc3c(cc21)CCC3]
or a pharmaceutically acceptable salt or stereoisomer thereof.
3. The compound of claim 1 that is:
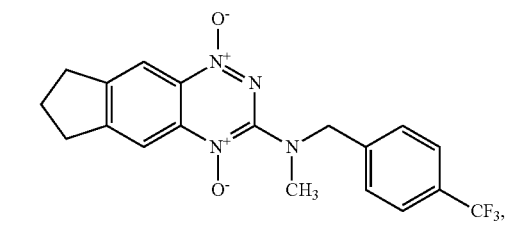 [SMILES: CN(Cc1ccc(C(F)(F)F)cc1)c1n[n+]([O-])c2cc3c(cc2[n+]1[O-])CCC3]
or a pharmaceutically acceptable salt or stereoisomer thereof.
4. A compound having a structure selected from the following table:
| | |
|---|---|
| SRI-012495 | 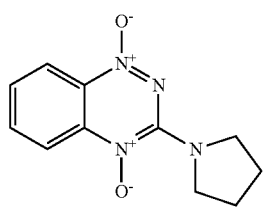 [SMILES: [O-][n+]1nc(N2CCCC2)[n+]([O-])c2ccccc21] |
| SRI-012530 | 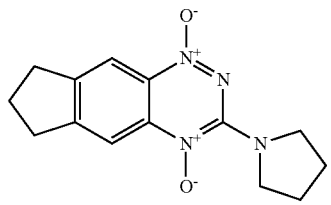 [SMILES: [O-][n+]1nc(N2CCCC2)[n+]([O-])c2cc3c(cc21)CCC3] |
| SRI-012562 | 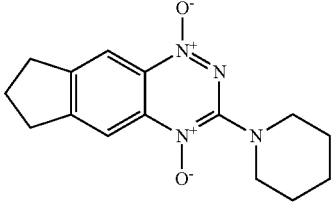 [SMILES: [O-][n+]1nc(N2CCCCC2)[n+]([O-])c2cc3c(cc21)CCC3] |
| SRI-012563 | 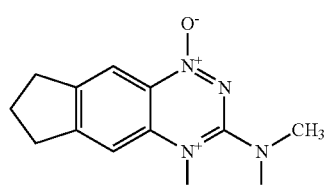 |
| SRI-012564 | 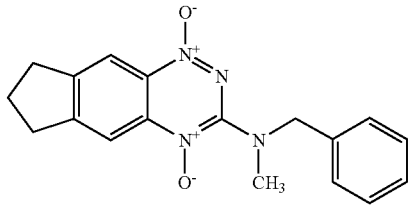 [SMILES: CN(Cc1ccccc1)c1n[n+]([O-])c2cc3c(cc2[n+]1[O-])CCC3] |

SRI-012565

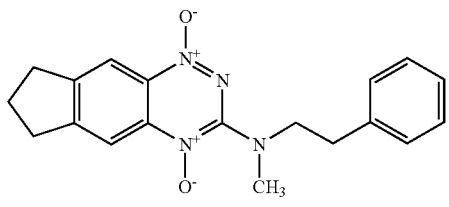 [SMILES: CN(CCc1ccccc1)c1n[n+]([O-])c2cc3c(cc2[n+]1[O-])CCC3]

SRI-012566

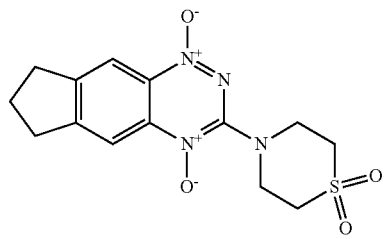 [SMILES: O=S1(=O)CCN(c2n[n+]([O-])c3cc4c(cc3[n+]2[O-])CCC4)CC1]

SRI-012567

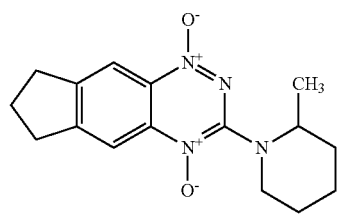 [SMILES: CC1CCCCN1c1n[n+]([O-])c2cc3c(cc2[n+]1[O-])CCC3]

SRI-012568

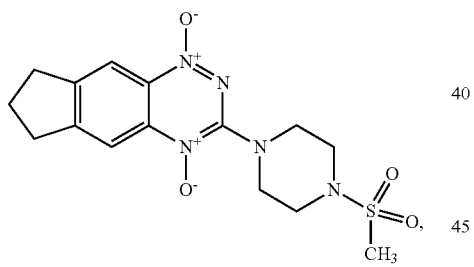

or a pharmaceutically acceptable salt or stereoisomer thereof.

5. The compound of claim 4 that is:

SRI-012495

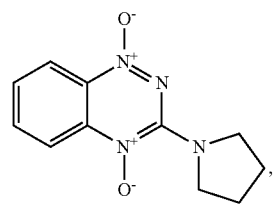

or a pharmaceutically acceptable salt or stereoisomer thereof.

6. The compound of claim 4 that is:

SRI-012530

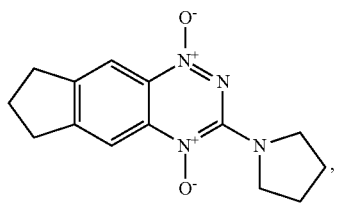

or a pharmaceutically acceptable salt or stereoisomer thereof.

7. The compound of claim 4 that is:

SRI-012562

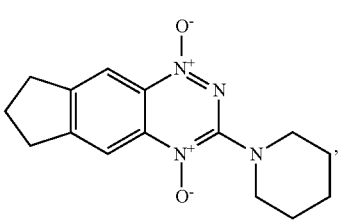

or a pharmaceutically acceptable salt or stereoisomer thereof.

8. The compound of claim 4 that is:

SRI-012563

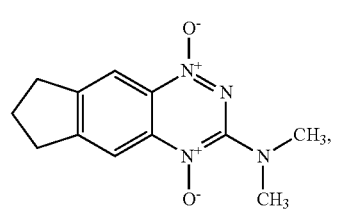

or a pharmaceutically acceptable salt or stereoisomer thereof.

9. The compound of claim 4 that is:

SRI-012564

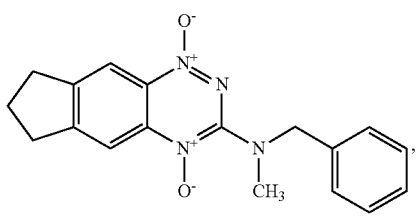

or a pharmaceutically acceptable salt or stereoisomer thereof.

10. The compound of claim 4 that is:

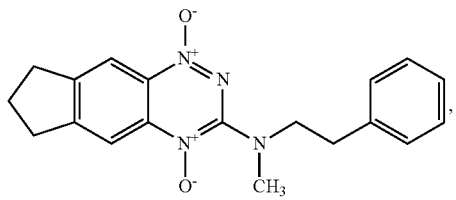

SRI-012565 or a pharmaceutically acceptable salt or stereoisomer thereof.

11. The compound of claim 4 that is:

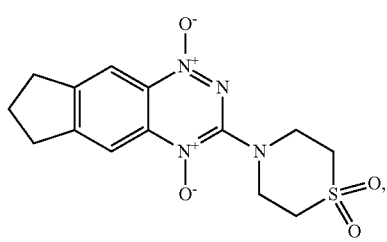

SRI-012566 or a pharmaceutically acceptable salt or stereoisomer thereof.

12. The compound of claim 4 that is:

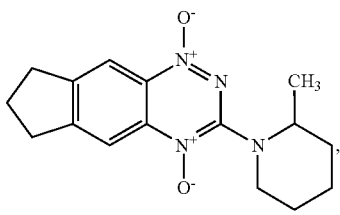

SRI-012567 or a pharmaceutically acceptable salt or stereoisomer thereof.

13. The compound of claim 4 that is:

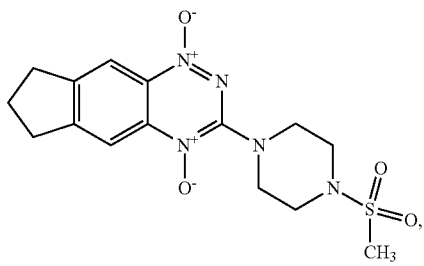 [SMILES: CS(=O)(=O)N1CCN(c2n[n+]([O-])c3cc4c(cc3[n+]2[O-])CCC4)CC1]

SRI-012568 or a pharmaceutically acceptable salt or stereoisomer thereof.

14. A pharmaceutical composition or kit comprising a compound of claim 1 and a second, different anti-*mycobacterium tuberculosis* (Mtb) drug.

15. A pharmaceutical composition or kit comprising a compound of claim 4 and a second, different anti-*mycobacterium tuberculosis* (Mtb) drug.

16. A method of making a compound of claim 1 according to the following scheme:

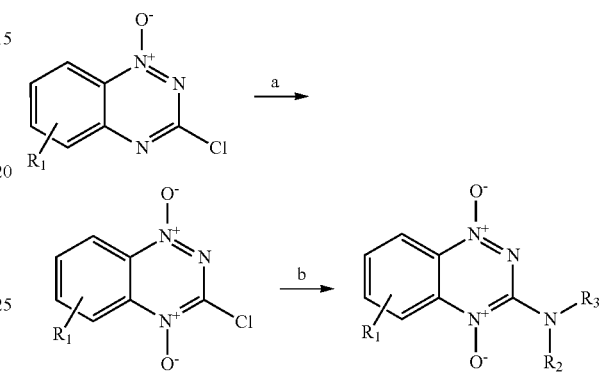

(a) HOFACN, DCM; b) $HNR_2R_3$, $Et_3N$, DCM; wherein X is $R_1$, W is N, A is $R_3$ and B is $R_2$.

17. A method of making a compound of claim 4 according to the following scheme:

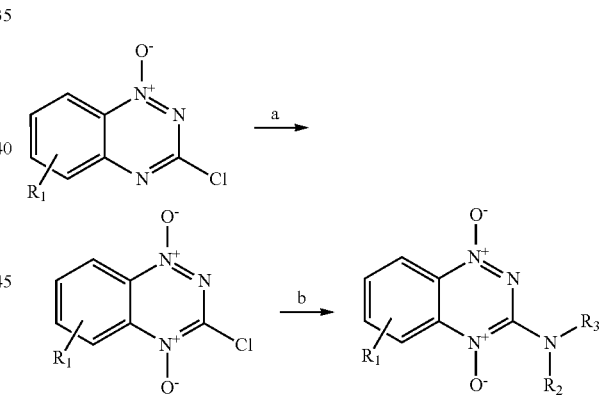

(a) HOFACN, DCM; b) $HNR_2R_3$, $Et_3N$, DCM; wherein X is $R_1$, W is N, A is $R_3$ and B is $R_2$.

18. A method of treating a *mycobacterium tuberculosis* (Mtb) infection, comprising: contacting a person in need thereof with an effective amount of compound of claim 1.

19. A method of treating a *mycobacterium tuberculosis* (Mtb) infection, comprising: contacting a person in need thereof with an effective amount of compound of claim 4.

* * * * *